United States Patent
Chen et al.

(10) Patent No.: US 10,035,817 B2
(45) Date of Patent: Jul. 31, 2018

(54) METHOD OF PURIFYING CELL-BINDING AGENT-CYTOTOXIC AGENT CONJUGATES WITH A PVDF MEMBRANE

(71) Applicant: ImmunoGen, Inc., Waltham, MA (US)

(72) Inventors: Xiaoxi Kevin Chen, Natick, MA (US); Xinfang Li, Newton, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 14/430,701

(22) PCT Filed: Oct. 4, 2013

(86) PCT No.: PCT/US2013/063480
§ 371 (c)(1),
(2) Date: Mar. 24, 2015

(87) PCT Pub. No.: WO2014/055877
PCT Pub. Date: Apr. 10, 2014

(65) Prior Publication Data
US 2015/0225446 A1    Aug. 13, 2015

Related U.S. Application Data

(60) Provisional application No. 61/709,891, filed on Oct. 4, 2012.

(51) Int. Cl.
| | |
|---|---|
| A61K 39/00 | (2006.01) |
| A61K 51/10 | (2006.01) |
| C07K 16/00 | (2006.01) |
| C07K 1/34 | (2006.01) |
| B01D 71/34 | (2006.01) |
| B01D 15/26 | (2006.01) |
| B01D 15/32 | (2006.01) |
| B01D 15/36 | (2006.01) |
| B01D 15/38 | (2006.01) |
| C07K 1/18 | (2006.01) |
| A61K 47/68 | (2017.01) |

(52) U.S. Cl.
CPC ............ *C07K 1/18* (2013.01); *A61K 47/6817* (2017.08); *B01D 15/265* (2013.01); *B01D 15/325* (2013.01); *B01D 15/327* (2013.01); *B01D 15/361* (2013.01); *B01D 15/3804* (2013.01); *B01D 71/34* (2013.01)

(58) Field of Classification Search
CPC .... A61K 39/00; A61K 51/1096; C07K 16/00; C07K 1/34; B01D 1/34; B01D 2315/16; B01D 15/361; B01D 15/3804; B01D 15/325; B01D 15/265; B01D 15/3277
See application file for complete search history.

(56) References Cited

U.S. PATENT DOCUMENTS

| | | |
|---|---|---|
| 4,137,230 A | 1/1979 | Hashimoto et al. |
| 4,149,003 A | 4/1979 | Carlsson et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,664,911 A | 5/1987 | Uhr et al. |
| 4,780,210 A | 10/1988 | Hsia |
| 4,859,449 A | 8/1989 | Mattes |
| 4,859,499 A | 8/1989 | Sauvinet et al. |
| 5,024,834 A | 6/1991 | Houston et al. |
| 5,208,020 A | 5/1993 | Chari et al. |
| 5,225,539 A | 7/1993 | Winter |
| 5,241,078 A | 8/1993 | Moreland et al. |
| 5,252,714 A | 10/1993 | Harris et al. |
| 5,416,064 A | 5/1995 | Chari et al. |
| 5,475,092 A | 12/1995 | Chari et al. |

(Continued)

FOREIGN PATENT DOCUMENTS

| | | |
|---|---|---|
| CA | 2006408 | 6/1990 |
| CN | 101267841 A | 9/2008 |

(Continued)

OTHER PUBLICATIONS

Cassidy et al., "Purification of *Staphylococcal* Alpha-Toxin by Adsorption Chromatography on Glass," *Infection and Immunity*, 13(3): 982-986 (1976).
Kahn et al., "Purification of Plasmid DNA by Tangential Flow Filtration," *Biotechnology and Bioengineering*, 69(1): 101-106 (2000).
U.S. Patent and Trademark Office, International Search Report and Written Opinion issued in International Patent Application No. PCT/US2013/63480, pp. 1-30 (dated Jan. 16, 2014).
Al-Arif et al., "Synthesis of fatty acyl CoA and other thiol esters using N-hydroxysuccinimide esters of fatty acids," *J. Lipid Research*, 10: 344-345 (1969).
Al-Katib et al., "Superior Antitumor Activity of SAR3419 to Rituximab in Xenograft Models for Non-Hodgkin's Lymphoma," *Clinical Cancer Research*, 15: 4038-4045 (2009).

(Continued)

*Primary Examiner* — Robert Landsman
*Assistant Examiner* — Bruce D Hissong
(74) *Attorney, Agent, or Firm* — Foley Hoag LLP; David P. Halstead

(57) ABSTRACT

The invention provides processes for preparing purified cell-binding agent cytotoxic agent conjugates comprising subjecting a mixture comprising a cell-binding agent cytotoxic agent conjugate and one or more impurities to a polyvinyl difluoride (PVDF) membrane to remove at least a portion of the impurities from the mixture, thereby providing a purified cell-binding agent cytotoxic agent conjugate.

90 Claims, 2 Drawing Sheets

(56) References Cited

U.S. PATENT DOCUMENTS

Figure 1A:
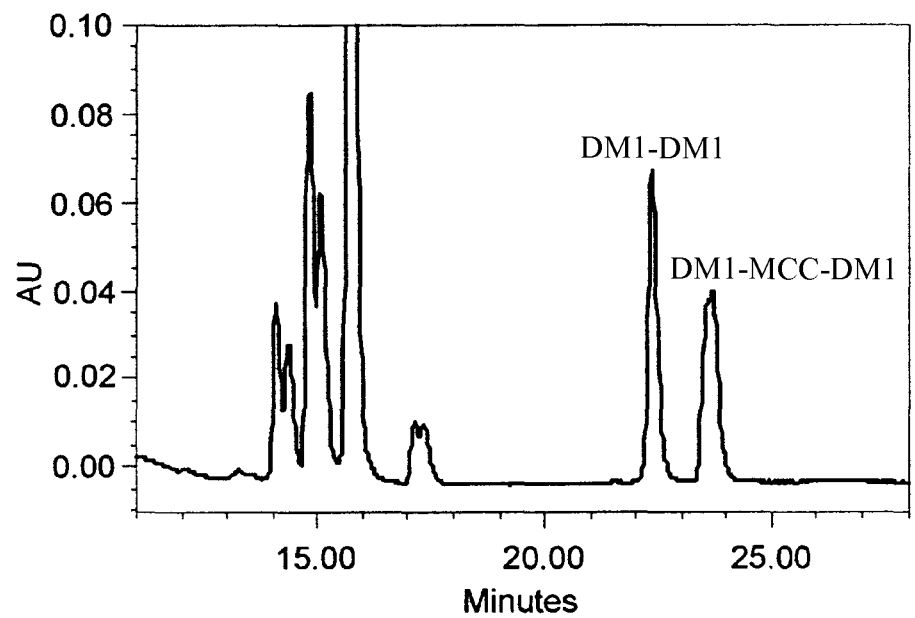

| | | |
|---|---|---|
| 5,529,986 A | 6/1996 | Larsson et al. |
| 5,545,806 A | 8/1996 | Lonberg et al. |
| 5,552,293 A | 9/1996 | Lindholm et al. |
| 5,556,623 A | 9/1996 | Barton et al. |
| 5,569,825 A | 10/1996 | Lonberg et al. |
| 5,580,853 A | 12/1996 | Sytkowski |
| 5,585,089 A | 12/1996 | Queen et al. |
| 5,585,499 A | 12/1996 | Chari et al. |
| 5,612,474 A | 3/1997 | Patel |
| 5,639,641 A | 6/1997 | Pedersen et al. |
| 5,665,357 A | 9/1997 | Rose et al. |
| 5,693,761 A | 12/1997 | Queen et al. |
| 5,693,762 A | 12/1997 | Queen et al. |
| 5,714,149 A | 2/1998 | Rhind et al. |
| 5,714,352 A | 2/1998 | Jakobovits |
| 5,747,446 A | 5/1998 | Sytkowski |
| 5,846,545 A | 12/1998 | Chari et al. |
| 5,885,793 A | 3/1999 | Griffiths et al. |
| 5,919,758 A | 7/1999 | Sytkowski |
| 5,965,714 A | 10/1999 | Ryall |
| 5,969,108 A | 10/1999 | McCafferty et al. |
| 6,171,586 B1 | 1/2001 | Lam et al. |
| 6,235,716 B1 | 5/2001 | Ben-Sasson |
| 6,265,150 B1 | 7/2001 | Terstappen et al. |
| 6,316,003 B1 | 11/2001 | Frankel et al. |
| 6,333,410 B1 | 12/2001 | Chari et al. |
| 6,340,461 B1 | 1/2002 | Terman |
| 6,340,701 B1 | 1/2002 | Chari et al. |
| 6,371,975 B2 | 4/2002 | Cruise et al. |
| 6,372,738 B2 | 4/2002 | Chari et al. |
| 6,391,913 B1 | 5/2002 | Page et al. |
| 6,436,931 B1 | 8/2002 | Chari et al. |
| 6,441,163 B1 | 8/2002 | Chari et al. |
| 6,462,070 B1 | 10/2002 | Hasan et al. |
| 6,534,660 B1 | 3/2003 | Yongxin et al. |
| 6,573,245 B1 | 6/2003 | Marciani |
| 6,586,618 B1 | 7/2003 | Zhao et al. |
| 6,596,757 B1 | 7/2003 | Chari et al. |
| 6,630,579 B2 | 10/2003 | Chari et al. |
| 6,632,979 B2 | 10/2003 | Erickson et al. |
| 6,706,708 B2 | 3/2004 | Chari et al. |
| 6,716,821 B2 | 4/2004 | Zhao et al. |
| 6,756,397 B2 | 6/2004 | Zhao et al. |
| 6,875,886 B2 | 4/2005 | Frangioni |
| 6,913,748 B2 | 7/2005 | Widdison |
| 7,045,605 B2 | 5/2006 | Bander et al. |
| 7,097,840 B2 | 8/2006 | Erickson et al. |
| 7,196,073 B2 | 3/2007 | Marciani |
| 7,368,565 B2 | 5/2008 | Chari et al. |
| 7,575,748 B1 | 8/2009 | Erickson et al. |
| 7,642,044 B2 | 1/2010 | Thogersen |
| 7,811,572 B2 | 10/2010 | Dai et al. |
| 7,964,415 B2 | 6/2011 | Zhelev et al. |
| 8,088,387 B2 | 1/2012 | Steeves et al. |
| 8,206,901 B2 | 6/2012 | Freskgard et al. |
| 8,383,122 B2 | 2/2013 | Dai et al. |
| 8,557,966 B2 | 10/2013 | Ab et al. |
| 8,624,003 B2 | 1/2014 | Kellogg et al. |
| 8,795,673 B2 | 8/2014 | Li et al. |
| 8,840,877 B2 | 9/2014 | Adamson et al. |
| 8,933,205 B2 | 1/2015 | Dai et al. |
| 9,376,500 B2 | 6/2016 | Kellogg et al. |
| 9,428,543 B2 | 8/2016 | Li et al. |
| 9,771,432 B2 | 9/2017 | Kellogg et al. |
| 9,789,204 B2 | 10/2017 | Dai et al. |
| 2002/0001587 A1 | 1/2002 | Erickson et al. |
| 2002/0150585 A1 | 10/2002 | Marciani et al. |
| 2002/0197266 A1 | 12/2002 | Debinski |
| 2003/0004210 A1 | 1/2003 | Chari et al. |
| 2003/0055226 A1 | 3/2003 | Chari et al. |
| 2003/0195365 A1 | 10/2003 | Zhao et al. |
| 2004/0024049 A1 | 2/2004 | Baloglu et al. |
| 2004/0192900 A1 | 9/2004 | Kunz et al. |
| 2004/0220142 A1 | 11/2004 | Marciani |
| 2004/0235840 A1 | 11/2004 | Chari et al. |
| 2004/0241174 A1 | 12/2004 | Amphlett et al. |
| 2005/0031627 A1 | 2/2005 | Mazzola et al. |
| 2005/0053608 A1 | 3/2005 | Weber et al. |
| 2005/0074425 A1 | 4/2005 | Waugh et al. |
| 2005/0112130 A1 | 5/2005 | Bhat et al. |
| 2005/0118183 A1 | 6/2005 | Hoffee et al. |
| 2005/0169933 A1 | 8/2005 | Steeves et al. |
| 2005/0175619 A1 | 8/2005 | Duffy et al. |
| 2005/0261232 A1 | 11/2005 | Strong et al. |
| 2006/0024317 A1 | 2/2006 | Boyd et al. |
| 2006/0062786 A1 | 3/2006 | Salcedo et al. |
| 2006/0073528 A1 | 4/2006 | Lecerf et al. |
| 2006/0099592 A1 | 5/2006 | Freskgard et al. |
| 2006/0100163 A1 | 5/2006 | Orlando et al. |
| 2006/0153834 A1 | 7/2006 | Carbonell et al. |
| 2006/0182740 A1 | 8/2006 | Yang et al. |
| 2006/0182750 A1 | 8/2006 | Chari et al. |
| 2006/0193865 A1 | 8/2006 | Govindan |
| 2006/0233811 A1 | 10/2006 | Chari |
| 2007/0031402 A1 | 2/2007 | Zhang et al. |
| 2007/0048314 A1 | 3/2007 | Dai et al. |
| 2007/0154901 A1 | 7/2007 | Thogersen et al. |
| 2007/0155750 A1 | 7/2007 | Neamati et al. |
| 2007/0196275 A1 | 8/2007 | Li et al. |
| 2007/0264257 A1 | 11/2007 | Dunussi-Joannopoulos et al. |
| 2008/0166363 A1 | 7/2008 | Govindan et al. |
| 2008/0171040 A1 | 7/2008 | Ebens et al. |
| 2008/0171865 A1 | 7/2008 | Steeves et al. |
| 2008/0213349 A1 | 9/2008 | Thakker et al. |
| 2008/0279868 A1 | 11/2008 | Boyd et al. |
| 2008/0305044 A1 | 12/2008 | McDonagh et al. |
| 2009/0274713 A1 | 11/2009 | Chari et al. |
| 2010/0003719 A1 | 1/2010 | Thogersen et al. |
| 2010/0047257 A1 | 2/2010 | Blanc et al. |
| 2010/0203007 A1 | 8/2010 | Li et al. |
| 2010/0291021 A1 | 11/2010 | Vetter et al. |
| 2010/0316656 A1 | 12/2010 | Bouchard et al. |
| 2011/0003969 A1 | 1/2011 | Kellogg et al. |
| 2011/0021744 A1 | 1/2011 | Dai et al. |
| 2011/0064754 A1 | 3/2011 | Taylor et al. |
| 2011/0166319 A1 | 7/2011 | Dai et al. |
| 2011/0206658 A1 | 8/2011 | Crowley et al. |
| 2011/0223257 A1 | 9/2011 | Zhao et al. |
| 2012/0149732 A1 | 6/2012 | Chucholowski et al. |
| 2012/0225089 A1 | 9/2012 | Bouchard et al. |
| 2012/0226026 A1 | 9/2012 | Singh et al. |
| 2012/0238731 A1 | 9/2012 | Fishkin et al. |
| 2012/0253021 A1 | 10/2012 | Li et al. |
| 2012/0259100 A1 | 10/2012 | Jin |
| 2012/0282175 A1 | 11/2012 | Carrigan et al. |
| 2013/0071482 A1 | 3/2013 | Bae et al. |
| 2013/0281678 A1 | 10/2013 | Dai et al. |
| 2014/0179906 A1 | 6/2014 | Kellogg et al. |
| 2014/0309406 A1 | 10/2014 | Li et al. |
| 2014/0350228 A1 | 11/2014 | Liu et al. |
| 2015/0010494 A1 | 1/2015 | Adamson et al. |
| 2015/0182635 A1 | 7/2015 | Dai et al. |
| 2015/0225446 A1 | 8/2015 | Chen et al. |
| 2015/0297742 A1 | 10/2015 | Strieker et al. |
| 2015/0306242 A1 | 10/2015 | Li et al. |
| 2015/0307596 A1 | 10/2015 | Li et al. |

FOREIGN PATENT DOCUMENTS

| | | |
|---|---|---|
| EP | 0 239 400 A2 | 9/1987 |
| EP | 0 425 235 A2 | 5/1991 |
| EP | 0 457 250 A2 | 11/1991 |
| EP | 0 485 749 A2 | 5/1992 |
| EP | 1 258 255 A1 | 11/2002 |
| EP | 2 468 304 A2 | 6/2012 |
| GB | 2 188 638 A | 10/1987 |
| JP | H03-161490 A | 7/1991 |
| JP | H04-266829 A | 9/1992 |
| JP | 2000-026404 A | 1/2000 |
| JP | 2004-532639 A | 10/2004 |
| JP | 2009-506032 A | 3/2007 |
| JP | 2008-505853 A | 2/2008 |
| WO | WO 92/01047 A1 | 1/1992 |
| WO | WO 96/39183 A1 | 12/1996 |

(56) References Cited

FOREIGN PATENT DOCUMENTS

| | | |
|---|---|---|
| WO | WO 99/05317 A1 | 2/1999 |
| WO | WO 99/06587 A2 | 2/1999 |
| WO | WO 00/02587 A1 | 1/2000 |
| WO | WO 00/66091 | 11/2000 |
| WO | WO 01/24763 A2 | 4/2001 |
| WO | WO 02/16368 A1 | 2/2002 |
| WO | WO 02/16401 A2 | 2/2002 |
| WO | WO 02/060955 A2 | 8/2002 |
| WO | WO 02/092127 A1 | 11/2002 |
| WO | WO 02/094325 A2 | 11/2002 |
| WO | WO 02/098883 A1 | 12/2002 |
| WO | WO 02/098887 A1 | 12/2002 |
| WO | WO 02/098897 A2 | 12/2002 |
| WO | WO 03/053462 A2 | 7/2003 |
| WO | WO 03/057163 A2 | 7/2003 |
| WO | WO 03/092623 A2 | 11/2003 |
| WO | WO 03/102132 A2 | 12/2003 |
| WO | WO 2004/103272 A2 | 12/2004 |
| WO | WO 2004/110498 A2 | 12/2004 |
| WO | WO 2005/037992 A2 | 4/2005 |
| WO | WO 2005/077090 A2 | 8/2005 |
| WO | WO 2005/094882 A | 10/2005 |
| WO | WO-2005/112919 A2 | 12/2005 |
| WO | WO 2005/117986 A2 | 12/2005 |
| WO | WO-2006/086733 A2 | 8/2006 |
| WO | WO 2006/113623 A2 | 10/2006 |
| WO | WO-2007/009229 A1 | 1/2007 |
| WO | WO 2007/024536 A2 | 3/2007 |
| WO | WO 2007/034495 A2 | 3/2007 |
| WO | WO 2008/057683 A2 | 5/2008 |
| WO | WO 2009/134952 A2 | 11/2009 |
| WO | WO2011/039724 * | 4/2011 |
| WO | WO 2011/106528 A1 | 9/2011 |
| WO | WO 2012/112687 A1 | 8/2012 |
| WO | WO 2012/112708 A1 | 8/2012 |
| WO | WO-2012/135517 A2 | 10/2012 |
| WO | WO-2014/055893 A1 | 4/2014 |

OTHER PUBLICATIONS

Baldus et al., "Lewis^y antigen (CD174) and apoptosis in gastric and colorectal carcinomas: correlations with clinical and prognostic parameters," *Histology and Histopathology*, 21: 503-510 (2006).
Berg et al., "The Purification of Proteins is an Essential First Step in Understanding Their Function," *Biochemistry*, 5$^{th}$ Ed., pp. 1-8, New York: WH Freeman (2002).
Bergelt et al., "Listeriolysin O as cytotoxic component of an immunotoxin," *Protein Science*, 18: 1210-1220 (2009).
Bhuyan et al., "CC-1065 (NSC 298223), a Most Potent Antitumor Agent: Kinetics of Inhibition of Growth, DNA Synthesis, and Cell Survival," *Cancer Research*, 42(9): 3532-3537 (1982).
Boger et al., "Synthesis and preliminary evaluation of (+)-CBI-indole$_2$: An enhanced functional analog of (+)-CC1065," *Bioorg. Med. Chem. Lett.*, 1: 115-120 (1991).
Boger et al., "Synthesis of N-(tert-butyloxycarbonyl)-CBI, CBI, CBI-CDPI$_1$, and CBI-CDPI$_2$: Enhanced Functional Analogs of CC-1065 Incorporating the 1,2,9,9a-Tetrahydrocyclopropa[c]benz[e]indol-4-one (CBI) Left-Hand Subunit," *J. Org. Chem.*, 55: 5823-5833 (1990).
Boschetti et al., "Antibody separation by hydrophobic charge induction chromatography," *Trends in Biotechnology*, 20(8): 333-337 (2002).
Brinkman et al., "A recombinant immunotoxin containing a disulfide-stabilized Fv fragment," *Proc. Natl. Acad. Sci. USA*, 90: 7538-7542 (1993).
Burgess, "The complex mediators of cell growth and differentiation," *Immunology Today*, 5(6): 155-158 (1984).
Carlsson et al., "Protein Thiolation and Reversible Protein-Protein Conjugation. N-Succinimidyl 3-(2-pyridyldithio)propionate, a new heterobifunctional reagent," *Biochem. J.*, 173: 723-737 (1978).
Chari et al., "Enhancement of the Selectivity and Antitumor Efficacy of a CC-1065 Analogue through Immunoconjugate Formation," *Cancer Research*, 55(18): 4079-4084 (1995).

Chari et al., "Immunoconjugates Containing Novel Maytansinoids: Promising Anticancer Drugs," *Cancer Research*, 52(1): 127-131 (1992).
Christy et al., "High-performance tangential flow filtration: a highly selective membrane separation process," *Desalination*, 144(1-3): 133-136 (2002).
Colomer et al., "Herceptin: From the Bench to the Clinic," *Cancer Invest.*, 19(1): 49-56 (2001).
Desmyter et al., "Crystal structure of a camel single-domain $V_H$ antibody fragment in complex with lysozyme," *Nature Struct. Biol.*, 3(9): 803-811 (1996).
Erickson et al., "Antibody-Maytansinoid Conjugates Are Activated in Targeted Cancer Cells by Lysosomal Degradation and Linker-Dependent Intracellular Processing," *Cancer Research*, 66(8): 4426-4433 (2006).
European Patent Office, International Search Report and Written Opinion issued in International Patent Application No. PCT/US2006/031653, pp. 1-22 (dated Apr. 3, 2007).
European Patent Office, International Search Report and Written Opinion issued in International Patent Application No. PCT/US2006/004937, pp. 1-27 (dated Apr. 11, 2007).
European Patent Office, International Search Report and Written Opinion issued in International Patent Application No. PCT/US12/31253, pp. 1-13 (dated Dec. 7, 2012).
European Patent Office, International Search Report and Written Opinion issued in International Patent Application No. PCT/US12/031243, pp. 1-11 (dated Dec. 10, 2012).
European Patent Office, Extended European Search Report issued in European Patent Application No. 10783998.7, pp. 1-7 (dated May 28, 2015).
European Patent Office, Extended European Search Report issued in European Patent Application No. 12856692.4, pp. 1-6 (dated Jul. 3, 2015).
Gao et al., "Expression of Lewis y antigen and integrin αv, β3 in ovarian cancer and their relationship with chemotherapeutic drug resistance," *J. Experimental & Clinical Cancer Research*, 32(36): 1-7 (2013).
Ghetie et al., "Large scale preparation of immunotoxins constructed with the Fab' fragment of IgG1 murine monoclonal antibodies and chemically deglycosylated ricin A chain," *J. Immunological Methods*, 111(2): 267-277 (1988).
Gong et al., "Comparison of DNA immobilization efficiency on new and regenerated commercial amine-reactive polymer microarray surfaces," *Surface Science*, 570: 67-77 (2004).
Greenberg et al., "A new antigen receptor gene family that undergoes rearrangement and extensive somatic diversification in sharks," *Nature*, 374: 168-173 (1995).
Griffin et al., "A monoclonal antibody reactive with normal and leukemic human myeloid progenitor cells," *Leukemia Res.*, 8(4): 521-534 (1984).
Haskard et al., "The Production of Human Monoclonal Autoantibodies from Patients with Rheumatoid Arthritis by the EBV-Hybridoma Technique," *J. Immunol. Methods*, 74(2): 361-367 (1984).
Heider et al., "Splice Variants of the Cell Surface Glycoprotein CD44 Associated with Metastatic Tumour Cells are Expressed in Normal Tissues of Humans and Cynomolgus Monkeys," *Eur. J. Cancer*, 31A(13/14): 2385-2391 (1995).
Henning, "Tumor cell targeted gene delivery by adenovirus 5 vectors carrying knobless fibers with antibody-binding domains," *Gene Therapy*, 12(3): 211-224 (2005).
Hurwitz et al., "The Covalent Binding of Daunomycin and Adriamycin to Antibodies, with Retention of Both Drug and Antibody Activities," *Cancer Research*, 35: 1175-1181 (1975).
Huse et al., "Generation of a Large Combinatorial Library of the Immunoglobulin Repertoire in Phage Lambda," *Science*, 246: 1275-1281 (1989).
Jensen et al., "Targeting the neural cell adhesion molecule in cancer," *Cancer Letters*, 258: 9-21 (2007).
Kawai et al., "Chemical Modification of Ansamitocins. III. Synthesis and Biological Effects of 3-Acyl Esters of Maytansinol," *Chemical and Pharmaceutical Bulletin*, 32(9): 3441-3451 (1984).

(56) References Cited

OTHER PUBLICATIONS

Kellogg et al., Antibody-maytansinoid conjugates with hydrophilic linkers: cytotoxic therapeutics with enhanced potency against cancer cells with low antigen number and multidrug resistance, *2009 AACR Annual Meeting*, Abstract 5480 (2009).
Kohler et al., "Derivation of specific antibody-producing tissue culture and tumor lines by cell fusion," *Eur. J. Immunol.*, 6: 511-519 (1976).
Kupchan et al., "Structural Requirements for Antileukemic Activity among the Naturally Occurring and Semisynthetic Maytansinoids," *J. Medicinal Chemistry*, 21(1): 31-37 (1978).
Ladino et al., "Folate-maytansinoids: target-selective drugs of low molecular weight," *International Journal of Cancer*, 73: 859-864 (1997).
Lewis et al., "An Improved Method for Conjugating Monoclonal Antibodies with N-Hydroxysulfosuccinimidyl DOTA," *Bioconjugate Chemistry*, 12(2): 320-324 (2001).
Liu et al., "Monoclonal Antibodies to the Extracellular Domain of Prostate-Specific Membrane Antigen Also React with Tumor Vascular Endothelium," *Cancer Res.*, 57(17): 3629-3634 (1997).
Liu et al., "Cure of human small cell lung cancer xenografts in SCID mice by a hN901-maytansinoid immunoconjugate," *Proc. Natl. Acad. Sci. USA*, 38(0): 29 (1997).
Liu et al., "Eradication of large colon tumor xenografts by targeted delivery of maytansinoids," *Proc. Natl. Acad. Sci. USA*, 93: 8618-8623 (1996).
Lundberg et al., "Click Assisted One-Pot Multi-Step Reactions in Polymer Science: Accelerated Synthetic Protocols," *Macromolecular Rapid Communications*, 29: 998-1015 (2008).
Maloney et al., "IDEC-C2B8 (Rituximab) Anti-CD20 Monoclonal Antibody Therapy in Patients With Relapsed Low-Grade Non-Hodgkin's Lymphoma," *Blood*, 90(6): 2188-2195 (1997).
Manosroi et al., "Thermo-stability and Antitumor Activity on Colon Cancer Cell Lines of Monoclonal Anti-CEA Antibody-Saporin Immunotoxin," *J. Korean Med. Sci.*, 7(2): 128-135 (1992).
Merriam-Webster, Online Dictionary, "Room Temperature" [retrieved at URL: http://www.merriam-webster.com/medical/room%20temperature on Dec. 12, 2014].
Nadler et al., "B4, a human B lymphocyte-associated antigen expressed on normal, mitogen-activated, and malignant B lymphocytes," *J. Immunol.*, 131: 244-250 (1983).
Nisonoff et al., "Separation of Univalent Fragments from the Bivalent Rabbit Antibody Molecule by Reduction of Disulfide Bonds," *Arch. Biochem. Biophys.*, 89: 230-244 (1960).
O'Keefe et al., "Characterization of a Transferrin-Diphtheria Toxin Conjugate," *J. Biol. Chem.*, 260(1): 932-937 (1985).
Okamoto et al., "Therapeutic Effect of Ansamitocin Targeted to Tumor by a Bispecific Monoclonal Antibody," *JP J. Cancer Research*, 83(7): 761-768 (1992).
Parham, "On the fragmentation of monoclonal IgG1, IgG2a, and IgG2b from BALB/c mice," *J. Immunol.*, 131: 2895-2902 (1983).
Pastan et al., "Characterization of Monoclonal Antibodies B1 and B3 That React with Mucinous Adenocarcinomas," *Cancer Research*, 51: 3781-3787 (1991).
Pedersen et al., "Comparison of Surface Accessible Residues in Human and Murine Immunoglobulin Fv Domains. Implication for Humanization of Murine Antibodies," *J. Mol. Biol.*, 235: 959-973 (1994).
Pietersz, "The Linkage of Cytotoxic Drugs to Monoclonal Antibodies for the Treatment of Cancer," *Bioconjugate Chemistry*, 1(2): 89-94 (1990).
Reider et al., "Maytansinoids," *The Alkaloids, XXIII*, 71-73 (1984).
Reiter et al., "Engineering interchain disulfide bonds into conserved framework regions of Fv fragments: improved biochemical characteristics of recombinant immunotoxins containing disulfide-stabilized Fv," *Protein Engineering*, 7: 697-704 (1994).
Ritz et al., "A monoclonal antibody to human acute lymphoblastic leukaemia antigen," *Nature*, 283: 583-585 (1980).
Roder et al., "The EBV-Hybridoma Technique," *Methods Enzymol*, 121: 140-167 (1986).
Roguska et al., "Humanization of murine monoclonal antibodies through variable domain resurfacing," *Proc. Natl. Acad. Sci. USA*, 91: 969-973 (1994).
Sehgal et al., "A Method for the High Efficiency of Water-Soluble Carbodiimide-Mediated Amidation," *Analytical Biochemistry*, 218: 87-91 (1994).
Smith, "Technology evaluation: C242-DM1, ImmunoGen Inc," *Current Opinion in Molecular Therapeutics*, 3(2): 198-203 (2001).
Spring et al., "Allotypic markers on Fab fragments of mouse immunoglobulins," *J. Immunol.*, 113: 470-478 (1974).
Stanfield et al., "Crystal Structure of a Shark Single-Domain Antibody V Region in Complex with Lysozyme," *Science*, 305: 1770-1773 (2004).
Stryer et al., "Levels of structure in protein architecture," *Biochemistry*, $3^{rd}$ Ed., pp. 31-33, New York: WH Freeman (1998).
Sytkowski et al., "Human erythropoietin dimers with markedly enhanced in vivo activity," *Proc. Natl. Acad. Sci. USA*, 95: 1184-1188 (1998).
Taylor-Papadimitriou et al., "Monoclonal antibodies to epithelium-specific components of the human milk fat globule membrane: production and reaction with cells in culture," *Int. J. Cancer*, 25: 17-21 (1981).
Thermo Scientific, Instructions for SMCC and Sulfo-SMCC, pp. 1-4 (2007).
Trouet et al., "A covalent linkage between daunorubicin and proteins that is stable in serum and reversible by lysosomal hydrolases, as required for a lysosomotropic drug-carrier conjugate: in vitro and in vivo studies," *Proc. Natl. Acad. Sci. USA*, 79: 626-629 (1982).
U.S. Patent and Trademark Office, International Search Report issued in International Patent Application No. PCT/US2002/03378, p. 1 (dated Jun. 12, 2002).
U.S. Patent and Trademark Office, International Search Report and Written Opinion issued in International Patent Application No. PCT/US10/37046, pp. 1-8 (dated Jul. 30, 2010).
U.S. Patent and Trademark Office, International Search Report and Written Opinion issued in International Patent Application No. PCT/US2012/069527, pp. 1-30 (dated Feb. 20, 2013).
U.S. Patent and Trademark Office, International Search Report and Written Opinion issued in International Patent Application No. PCT/US2013/63503, pp. 1-18 (dated Jan. 16, 2014).
U.S. Patent and Trademark Office, International Search Report and Written Opinion issued in International Patent Application No. PCT/US2013/63415, pp. 1-28 (dated Jan. 29, 2014).
Ugwu et al., "The Effect of Buffers on Protein Conformational Stability," *Pharmaceutical Technology*, pp. 86, 88, 90, 92, 94, 96, 98, 100, 102, 104, 106, 108, 100-113 (2004).
Umemoto et al., "Preparation and in vitro cytotoxicity of a methotrexate-anti-MM46 monoclonal antibody conjugate via an oligopeptide spacer," *Int. J. Cancer*, 43(4): 677-684 (1989).
Van Hof et al., "Biodistribution of [111]Indium-labeled Engineered Human Antibody CTMO1 in Ovarian Cancer Patients: Influence of Protein Dose," *Cancer Res.*, 56(22): 5179-5185 (1996).
Wang et al., "Trichosanthin-monoclonal Antibody Conjugate Specifically Cytotoxic to Human Hepatoma Cells in Vitro," *Cancer Res.*, 51: 3353-3355 (1991).
Warpehoski et al., "Stereoelectronic Factors Influencing the Biological Activity and DNA Interaction of Synthetic Antitumor Agents Modeled on CC-1065," *J. Med. Chem*, 31: 590-603 (1988).
Wawrzynczak et al., "Molecular and biological properties of an abrin A chain immunotoxin designed for therapy of human small cell lung cancer," *Br. J. Cancer*, 66(2): 361-366 (1992).
Welt et al., "Antibody Targeting in Metastatic Colon Cancer: A Phase I Study of Monoclonal Antibody F19 Against a Cell-Surface Protein of Reactive Tumor Stromal Fibroblasts," *J. Clin. Oncol.*, 12(6): 1193-1203 (1994).
Winkler et al., "Changing the antigen binding specificity by single point mutations of an anti-p24 (HIV-1) antibody," *J. Immunology*, 165(8): 4505-4514 (2000).
Yan et al., "Enhancement of the adhesive and spreading potentials of ovarian carcinoma RMG-1 cells due to increased expression of integrin $\alpha5\beta1$ with the Lewis Y-structure on transfection of the $\alpha1,2$-fucosyltransferase gene," *Biochimie*, 92: 852-857 (2010).

(56) References Cited

OTHER PUBLICATIONS

Chen et al., "Factors affecting endotoxin removal from recombinant therapeutic proteins by anion exchange chromatography" *Protein Expression and Purification*, 64: 76-81 (2009).

McDonagh et al., "Engineered anti-CD70 antibody-drug conjugate with increased therapeutic index," *Mol. Cancer Ther.*, 7(9): 2913-2923 (2008).

Reis et al., "High-performance tangential flow filtration using charged membranes," *J. of Membrane Science*, 159: 133-142 (1999).

Tugcu et al., Maximizing Productivity of Chromatography Steps for Purification of Monoclonal Antibodies, *Biotechnology and Bioengineering*, 99(3): 599-613 (2008).

Zhou et al., "New Q Membrane Scale-Down Model for Process-Scale Antibody Purification," *Journal of Chromatography A*, 1134: 66-73 (2006).

European Patent Office, Extended European Search Report issued in European Patent Application No. 13843881.7, pp. 1-8 (dated Apr. 11, 2016).

"Clinical Trials Begin of Antiangiogenesis Antibody, CNTO 95," Cancer Weekly, 57 (Jan. 13, 2004).

European Search Report issued by the European Patent Office in corresponding Application No. 13844268.6, dated Apr. 3, 2017.

Jayson et al., "Phase I Study of CNTO 95, a Fully Human Monoclonal Antibody (mAb) to alphav Integrins, in Patients with Solid Tumors," J Clin Oncol, 22(14): 3119 (2004).

Jiao et al., "Pharmacokinetics of CNTO 95, a Fully Human MAB to Human Integrin Receptors Following Single or Multiple IV Injections to Cynomolgus Monkeys," Eur J Cancer, 2(8): 93 (2004).

Trikha et al., "CNTO 95, a Fully Human Monoclonal Antibody that Inhibits alphav Integrins, Has Antitumor and Antiangiogenic Activity in Vivo," Int J Cancer, 110(3): 326-335 (2004).

Written Opinion and International Search Report dated Jul. 30, 2010, as issued in International Patent Application No. PCT/US10/37046, filed Jun. 2, 2010.

\* cited by examiner

SEQUENCE LISTING

```
<160> NUMBER OF SEQ ID NOS: 4

<210> SEQ ID NO 1
<211> LENGTH: 450
<212> TYPE: PRT
<213> ORGANISM: Artificial Sequence
<220> FEATURE:
<223> OTHER INFORMATION: Synthetic sequence
```

```
<400> SEQUENCE: 1

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                    405                 410                 415
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 211
<212> TYPE: PRT
<213> ORGANISM: Artificial Sequence
<220> FEATURE:
<223> OTHER INFORMATION: Synthetic Sequence

<400> SEQUENCE: 2

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 3
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 3

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30
```

```
Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Pro Ser Leu Lys
        50                  55                  60

Ser Arg Leu Ser Ile Lys Lys Asp His Ser Lys Ser Gln Val Phe Leu
65                   70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
                100                 105                 110

Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 4

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
                100                 105
```

METHOD OF PURIFYING CELL-BINDING AGENT-CYTOTOXIC AGENT CONJUGATES WITH A PVDF MEMBRANE

CROSS-REFERENCE TO RELATED APPLICATIONS

This patent application claims the benefit of U.S. Provisional Patent Application No. 61/709,891, filed Oct. 4, 2012, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,306 Byte ASCII (Text) file named "720216SequenceListing.txt," created on Mar. 19, 2015.

BACKGROUND OF THE INVENTION

Antibody-drug conjugates which are useful for the treatment of cancer and other diseases are commonly composed of three distinct elements: a cell-binding agent; a linker; and a cytotoxic agent. One of the commonly used manufacturing processes comprises a modification step, in which the cell-binding agent is reacted with a bifunctional linker to form a cell-binding agent covalently attached to a linker having a reactive group, a purification step in which the modified antibody is purified from the other components of the modification reaction, a conjugation step, in which the modified cell-binding agent is reacted with a cytotoxic agent to form a covalent chemical bond from the linker (using the reactive group) to the cytotoxic agent, and a second purification step, in which the conjugate is purified from the other components of the conjugation reaction.

Recent clinical trials have shown a promising role for antibody-drug conjugates in the treatment of many different types of cancers. Therefore, there is a need to produce conjugates of high purity and high stability that can be used to treat patients. Despite advances in preparing antibody-drug conjugates, current processes are limited by several factors. For example, the conjugates produced by these processes comprise an increased amount of impurities, including free cytotoxic agent (e.g., cytotoxic agent dimer related species) and/or high molecular weight species (e.g., dimers and other higher order aggregates). Current purification methods employed in the art, such as tangential flow filtration and adsorptive chromatography, do not efficiently remove these impurities without significantly decreasing the yield and/or are cumbersome for large scale manufacturing processes.

Thus, there remains a need for improved processes of preparing antibody-drug conjugates that are more stable and are of higher purity than antibody-drug conjugates produced by current processes. The invention provides such a process. These and other advantages of the invention, as well as additional inventive features, will be apparent from the description of the invention provided herein.

BRIEF SUMMARY OF THE INVENTION

The invention provides processes for preparing purified cell-binding agent cytotoxic agent conjugates comprising subjecting a mixture comprising a cell-binding agent cytotoxic agent conjugate and one or more impurities to a polyvinyl difluoride (PVDF) membrane to remove at least a portion of the impurities from the mixture, thereby providing a purified cell-binding agent cytotoxic agent conjugate. The present invention also includes a conjugate comprising a cell-binding agent chemically coupled to a cytotoxic agent prepared according to the processes described herein.

BRIEF DESCRIPTION OF THE SEVERAL VIEWS OF THE DRAWING(S)

Figure 1B:
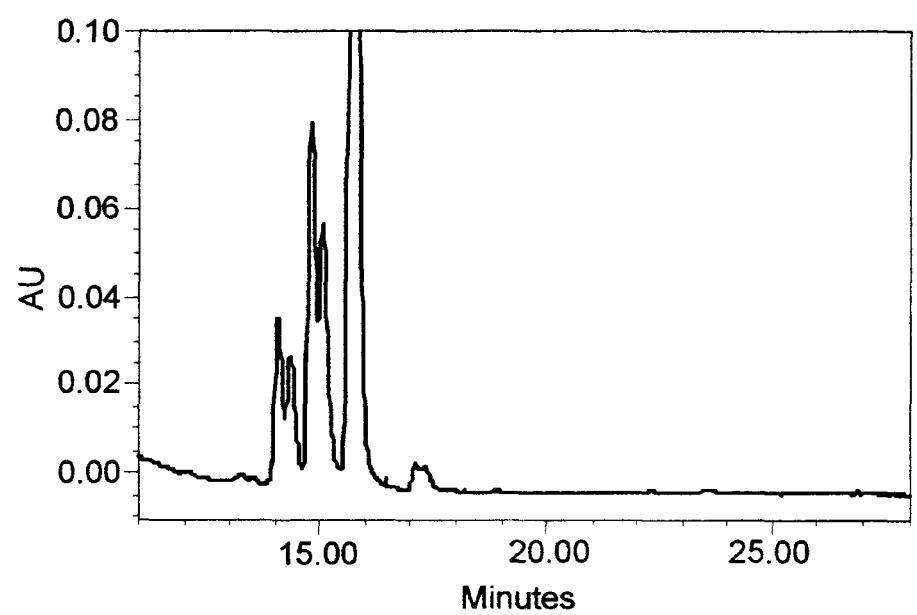

FIGS. 1A-B are chromatograms depicting the species present in an antibody-SMCC-DM1 conjugate reaction mixture before (FIG. 1A) and after (FIG. 1B) PVDF filtration.

Figure 2:
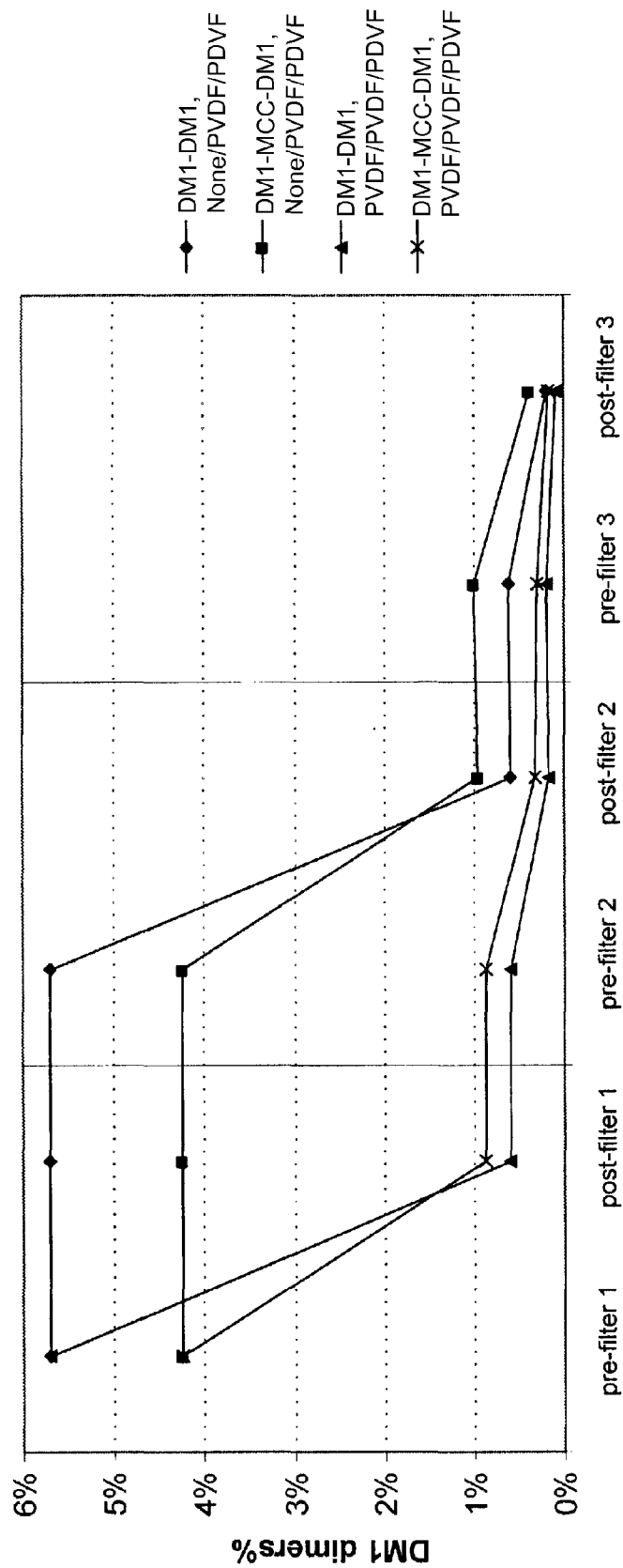

FIG. 2 is a line graph depicting the percent of DM1 dimer species (y-axis) present in an antibody-SMCC-DM1 conjugate reaction mixture before and after filtration through multiple PVDF membranes (x-axis).

DETAILED DESCRIPTION OF THE INVENTION

One of ordinary skill in the art will appreciate that conjugates comprising a cell-binding agent, such as an antibody, chemically coupled to a cytotoxic agent ("antibody-cytotoxic agent conjugates") typically are prepared by modifying an antibody with a bifunctional crosslinking reagent at a low pH (i.e., pH 7.0 or below), purifying the antibody having linkers bound thereto, conjugating a cytotoxic agent to the antibody having linkers bound thereto, and purifying the antibody-cytotoxic agent conjugate. Recently, methods have been developed to produce conjugates of increased stability by maximizing the amount of linker stably bound to the cell-binding agent and minimizing undesirable side reactions that lead to conjugate instability. For example, methods have been developed in which the process for making the conjugate is performed in one step (see. e.g., the processes described in U.S. Patent Application Publication No. 2012/0253021) and/or at a high pH (e.g., a pH of 7 or higher) (see, e.g., the processes described International Patent Application Publication No. WO 2012/135522) in order to increase the level of desirable species of cell-binding agents having a linker stably bound thereto and reduce the level of undesirable reaction products (e.g., cell-binding agents having a linker unstably bound thereto). Although such processes produce conjugates of increased stability, it has been discovered that these processes result in conjugates having an increased levels of impurities, such as free cytotoxic agent (e.g., cytotoxic agent dimer related species) and/or high molecular weight species (e.g., dimers and other higher order aggregates). Current purification methods employed in the art, such as tangential flow filtration and adsorptive chromatography, do not efficiently remove these impurities without significantly decreasing the yield and/or are cumbersome for large scale manufacturing processes.

It was surprisingly discovered that a polyvinyl difluoride (PVDF) membrane can be used to remove at least a portion of the impurities from a mixture comprising a cell-binding agent cytotoxic agent conjugate. In particular, it was unexpectedly discovered that free cytotoxic agent (e.g., cytotoxic agent dimer related species) can be effectively and efficiently removed from a mixture comprising a cell-binding agent cytotoxic agent conjugate by subjecting the mixture to a PVDF membrane. Accordingly, the invention provides processes for manufacturing cell-binding agent-cytotoxic agent conjugates of increased purity and stability comprising subjecting a mixture comprising a cell-binding agent cytotoxic agent conjugate and one or more impurities to a PVDF membrane.

The invention provides a process for preparing a purified cell-binding agent cytotoxic agent conjugate comprising subjecting a mixture comprising a cell-binding agent cytotoxic agent conjugate and one or more impurities to a PVDF membrane to remove at least a portion of the impurities from the mixture, thereby providing a purified cell-binding agent cytotoxic agent conjugate. The PVDF membrane can be used to remove a variety of impurities commonly found in a mixture comprising a cell-binding agent cytotoxic agent conjugate. For example, the PVDF membrane can be used to remove one or more impurities selected from the group of cytotoxic agent dimers, aggregates of the cell-binding agent cytotoxic agent conjugate, free cytotoxic agent, unconjugated linker, and mixtures thereof.

In one embodiment, the mixture comprising a cell-binding agent cytotoxic agent conjugate comprises cytotoxic agent dimers as an impurity, and the PVDF membrane removes some portion of the cytotoxic agent dimers from the mixture to provide the purified cell-binding agent cytotoxic agent conjugate. In another embodiment, the mixture comprising a cell-binding agent cytotoxic agent conjugate comprises aggregates of the cell-binding agent cytotoxic agent conjugate as an impurity, and the PVDF membrane removes some portion of the aggregates of the cell-binding agent cytotoxic agent from the mixture to provide the purified cell-binding agent cytotoxic agent conjugate. In another embodiment, the mixture comprising a cell-binding agent cytotoxic agent conjugate comprises free cytotoxic agent as an impurity, and the PVDF membrane removes some portion of the free cytotoxic agent from the mixture to provide the purified cell-binding agent cytotoxic agent conjugate. In another embodiment, the mixture comprising a cell-binding agent cytotoxic agent conjugate comprises unconjugated linker as an impurity, and the PVDF membrane removes some portion of the unconjugated linker from the mixture to provide the purified cell-binding agent cytotoxic agent conjugate.

In a preferred embodiment, the mixture comprising a cell-binding agent cytotoxic agent conjugate comprises cytotoxic agent dimers chemically coupled to each other through a linker (e.g., DM1-MCC-DM1, DM1-SPP-DM1, or DM1-CX1-1-DM1) as an impurity, and the PVDF membrane removes some portion of the cytotoxic agent dimers chemically coupled to each other through a linker (e.g., DM1-MCC-DM1, DM1-SPP-DM1, or DM1-CX1-1-DM1) from the mixture to provide the purified cell-binding agent cytotoxic agent conjugate. In another preferred embodiment, the mixture comprising a cell-binding agent cytotoxic agent conjugate comprises cytotoxic agent dimers that are not chemically coupled to each other through a linker (e.g., DM1-DM1) as an impurity, and the PVDF membrane removes some portion of the cytotoxic agent dimers that are not chemically coupled to each other through a linker (e.g., DM1-DM1) from the mixture to provide the purified cell-binding agent cytotoxic agent conjugate.

When the mixture comprising a cell-binding agent cytotoxic agent conjugate and one or more impurities is subjected to a PVDF membrane, the resulting purified cell-binding agent cytotoxic agent conjugate comprises a reduced level of at least one or more impurities as compared to the level of the one or more impurities in the mixture prior to subjecting the mixture to the PVDF membrane. For example, the PVDF membrane removes at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or even 100% of the one or more impurities in the mixture as compared to the level of the one or more impurities in the mixture prior to subjecting the mixture to the PVDF membrane. In one embodiment, the PVDF membrane removes about 10% to about 100%, about 10% to about 90%, about 20% to about 100%, about 20% to about 90%, about 20% to about 80%, about 30% to about 100%, about 30% to about 90%, about 30% to about 80%, about 40% to about 80%, about 40% to about 90%, about 40% to about 100%, about 50% to about 80%, about 50% to about 90%, about 50% to about 100% (e.g., about 60% to about 90%, about 70% to about 90%), about 60% to about 100%, about 70% to about 100%, about 80% to about 100%, about 90% to about 100%, or about 95% to about 100% (e.g., about 96% to about 100%, about 97% to about 100%, about 98% to about 100%, about 99% to about 100%, about 95% to about 96%, about 95% to about 97%, about 95% to about 98%, or about 95% to about 99%) of the one or more impurities in the mixture as compared to the level of the one or more impurities in the mixture prior to subjecting the mixture to the PVDF membrane.

In one embodiment, the pH of the mixture comprising the cell-binding agent cytotoxic agent conjugate and one or more impurities is adjusted prior to subjecting the mixture to a PVDF membrane. The pH of the mixture comprising the cell-binding agent cytotoxic agent conjugate and one or more impurities preferably is about 4 to about 9 (e.g., a pH of about 4.5 to about 8.5, about 5 to about 8, about 5.5 to about 7.5, about 6 to about 7, about 6.5 to about 7.5, about 7 to about 8, about 8 to about 9, about 4.5 to about 6, or about 4.5 to about 5). In some embodiments, the pH of the mixture is about 6 to about 6.5 (e.g., a pH of 5.5 to 7, a pH of 5.7 to 6.8, a pH of 5.8 to 6.7, a pH of 5.9 to 6.6, or a pH of 6 to 6.5), a pH of about 6 or below (e.g., a pH of about 4 to 6, about 4 to about 5.5, about 4 to about 4.5, about 4 to about 5, about 5 to 6), or a pH of about 6.5 or greater (e.g., a pH of 6.5 to about 9, about 6.5 to about 7, about 7 to about 9, about 7.5 to about 9, or 6.5 to about 8). In one embodiment, the pH of the mixture is greater than 7.5 (e.g., a pH of 7.6 to about 9, 7.7 to about 9, about 7.8 to about 9, about 7.9 to about 9, 7.6 to about 8.5, 7.6 to about 8, 7.7 to about 8.5, 7.7 to about 8, about 7.8 to about 8.4, about 7.8 to about 8.2, about 8 to about 9, or about 8 to about 8.5). For example, the pH of the mixture can be a pH of 7.6, 7.7, 7.8, 7.9, 8, 8.1, 8.2, 8.3, 8.4, 8.5, 8.6, 8.7, 8.8, 8.9, or 9. In another embodiment, the pH of the mixture is about 4.8 (e.g., about 4.5 to about 5, about 4.6 to about 5, or about 4.7 to about 4.9).

A variety of PVDF membranes are known in the art and can be used in accordance with the invention described herein. In one embodiment, the PVDF membrane has a pore size of 0.22 microns. In another embodiment, the PVDF membrane has a pore size of 0.45 microns. In another embodiment, the PVDF membrane is a dual layer membrane having a pore size of 0.45 and 0.22 microns (i.e., a dual layer 0.45/0.22 micron pore size membrane pore size membrane).

In some embodiments, the PVDF membrane is gamma irradiated. In other embodiments, the PVDF membrane is not gamma irradiated.

A number of processes for preparing cell-binding agent-cytotoxic agent conjugates have been described (see, e.g., U.S. Patent Application Publication No. 2012/0253021; International Patent Application Publication No. WO 2012/135522; U.S. Pat. No. 5,208,020; U.S. Pat. No. 6,441,163;

U.S. Pat. No. 7,811,572; U.S. Patent Application Publication No. 2006/0182750; U.S. Patent Application Publication No. 2008/0145374; and U.S. Patent Application Publication No. 2011/0003969).

In one embodiment, the invention provides a process for preparing a conjugate comprising a cell-binding agent chemically coupled to a cytotoxic agent, wherein the modification reaction and the conjugation reaction are combined into a single step, followed by a purification step (i.e., the one-step process described in U.S. Patent Application Publication No. 2012/0253021), and wherein the process comprises subjecting the mixture comprising a cell-binding agent cytotoxic agent conjugate and one or more impurities to a PVDF membrane either before or after the purification step. The one-step process comprises contacting a cell-binding agent (e.g., an antibody) with a cytotoxic agent to form a first mixture comprising the cell-binding agent and the cytotoxic agent, and then contacting the first mixture comprising the cell-binding agent and the cytotoxic agent with a bifunctional crosslinking reagent comprising a linker, in a solution having a pH of about 4 to about 9 to provide a second mixture comprising the cell-binding agent cytotoxic agent conjugate and one or more impurities (e.g., free cytotoxic agent and reaction by-products), wherein the cell-binding agent is chemically coupled through the linker to the cytotoxic agent. The second mixture is then subjected to purification to provide a purified cell-binding agent cytotoxic agent conjugate. The second mixture comprising a cell-binding agent cytotoxic agent conjugate and one or more impurities is subjected to a PVDF membrane before the purification step, after the purification step, or both.

The one-step reaction preferably is performed at a pH of about 4 to about pH 9 (e.g., a pH of about 4.5 to about 8.5, about 5 to about 8, about 5.5 to about 7.5, about 6 to about 7, about 6 to about 8, about 6 to about 9, or about 6.5 to about 7.5). In some embodiments, the reaction is performed at a pH of about 6 to about 8 (e.g., a pH of about 6, about 6.5, about 7, about 7.5, or about 8).

In one embodiment, the reaction is performed at a pH of about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9. In another embodiment, the reaction is performed at a pH of about 7.5 to about 9, about 7.5 to about 8.5, about 7.5 to about 8, about 7.8 to about 9, about 7.8 to about 8.5, about 7.8 to about 8, about 8 to about 9, about 8 to about 8.5, or about 8.5 to about 9. In another embodiment the reaction is performed at a pH of about 7.8 (e.g., a pH of 7.6 to 8.0 or a pH of 7.7 to 7.9). In another embodiment, the modification reaction is performed at a pH of about 8 (e.g., a pH of 7.8 to 8.2 or a pH of 7.9 to 8.1).

In another embodiment, the reaction is performed at a pH that is greater than 7.5 (e.g., a pH of 7.6 to about 9, 7.7 to about 9, about 7.8 to about 9, about 7.9 to about 9, 7.6 to about 8.5, 7.6 to about 8, 7.7 to about 8.5, 7.7 to about 8, about 7.8 to about 8.4, about 7.8 to about 8.2, about 8 to about 9, or about 8 to about 8.5).

In one embodiment, the contacting is effected by providing the cell-binding agent, then contacting the cell-binding agent with the cytotoxic agent to form a first mixture comprising the cell-binding agent and the cytotoxic agent, and then contacting the first mixture comprising the cell-binding agent and the cytotoxic agent with the bifunctional crosslinking reagent. For example, in one embodiment, the cell-binding agent is provided in a reaction vessel, the cytotoxic agent is added to the reaction vessel (thereby contacting the cell-binding agent), and then the bifunctional crosslinking reagent is added to the mixture comprising the cell-binding agent and the cytotoxic agent (thereby contacting the mixture comprising the cell-binding agent and the cytotoxic agent). In one embodiment, the cell-binding agent is provided in a reaction vessel, and the cytotoxic agent is added to the reaction vessel immediately following providing the cell-binding agent to the vessel. In another embodiment, the cell-binding agent is provided in a reaction vessel, and the cytotoxic agent is added to the reaction vessel after a time interval following providing the cell-binding agent to the vessel (e.g., about 5 minutes, about 10 minutes, about 20 minutes, about 30 minutes, about 40 minutes, about 50 minutes, about 1 hour, about 1 day or longer after providing the cell-binding agent to the space). The cytotoxic agent can be added quickly (i.e., within a short time interval, such as about 5 minutes, about 10 minutes) or slowly (such as by using a pump).

The mixture comprising the cell-binding agent and the cytotoxic agent can be then contacted with the bifunctional crosslinking reagent either immediately after contacting the cell-binding agent with the cytotoxic agent or at some later point (e.g., about 5 minutes to about 8 hours or longer) after contacting the cell-binding agent with the cytotoxic agent. For example, in one embodiment, the bifunctional crosslinking reagent is added to the mixture comprising the cell-binding agent and the cytotoxic agent immediately after the addition of the cytotoxic agent to the reaction vessel comprising the cell-binding agent. Alternatively, the mixture comprising the cell-binding agent and the cytotoxic agent can be contacted with the bifunctional crosslinking reagent at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the cell-binding agent with the cytotoxic agent.

In another embodiment, the cytotoxic agent and the bifunctional agent are added through multiple cycles (e.g., 1, 2, 3, 4, 5 or more cycles). For example, the invention provides a process comprising the steps of: a) contacting a cell-binding agent with a cytotoxic agent to form a first mixture comprising the cell-binding agent and the cytotoxic agent; and then contacting the first mixture with a bifunctional crosslinking reagent comprising a linker, in a solution having a pH of about 4 to about 9 to provide a second mixture comprising the cell-binding agent cytotoxic agent conjugate and one or more impurities (e.g., free cytotoxic agent and reaction by-products), wherein the cell-binding agent is chemically coupled through the linker to the cytotoxic agent; b) contacting the second mixture with the cytotoxic agent to form a third mixture; and then contacting the third mixture with the bifunctional crosslinking reagent at a pH of about 4 to about 9 to provide a fourth mixture; and c) purifying the fourth mixture to provide the purified cell-binding agent cytotoxic agent conjugate. In one embodiment, step b) is carried out after a time interval (e.g., about 1 hour, about 2 hours, about 3 hours or longer) following step a). In another embodiment, step b) can be repeated several times (e.g., 1, 2, 3, 4 or more times) before step c) is carried out. The additional step b) can be carried out after a time interval (e.g., about 1 hour, about 2 hours, about 3 hours or longer) following the initial step b).

In another embodiment, the bifunctional crosslinking reagent is added before the complete addition of the cytotoxic agent. For example, in one embodiment, the cytotoxic agent is added to the cell-binding agent continuously over a time interval (e.g., over about 5 minutes, about 10 minutes, about 30 minutes, about 1 hour, about 2 hours, about 3 hours, or longer) to form a mixture comprising the cell-binding agent and the cytotoxic agent. Before the addition of the cytotoxic agent is complete, the bifunctional crosslinking reagent is added to the mixture comprising the cell-binding agent and the cytotoxic agent, provided that at any time, the cytotoxic agent is in molar excess of the bifunctional crosslinking reagent. In one embodiment, the bifunctional crosslinking reagent is added continuously over a time interval (e.g., over about 5 minutes, about 10 minutes, about 30 minutes, about 1 hour, about 2 hours, about 3 hours, or longer).

After the mixture comprising the cell-binding agent and the cytotoxic agent is contacted with the bifunctional crosslinking reagent, the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

Thus, in one embodiment, the invention provides a process for preparing a purified cell-binding agent cytotoxic agent conjugate comprising contacting a cell-binding agent with a cytotoxic agent to form a first mixture comprising the cell-binding agent and the cytotoxic agent, then contacting the first mixture with a bifunctional crosslinking reagent comprising a linker, in a solution having a pH of about 4 to about 9, to provide a second mixture comprising the cell-binding agent cytotoxic agent conjugate comprising the cell-binding agent chemically coupled through the linker to the cytotoxic agent and one or more impurities; (b) subjecting the second mixture to a polyvinyl difluoride (PVDF) membrane to remove at least a portion of the impurities, thereby providing a purified second mixture of the cell-binding agent cytotoxic agent conjugate; and (c) subjecting the purified second mixture after step (b) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture. Any purification method described herein can be used in the inventive process. In a preferred embodiment, tangential flow filtration, adsorptive chromatography, or non-adsorptive chromatography is utilized as the purification step.

In one embodiment of the invention, contacting a cell-binding agent with a bifunctional crosslinking reagent (i.e., the modification reaction) produces a first mixture comprising the cell-binding agent having linkers bound thereto and one or more impurities (e.g., reactants and other by-products). In some embodiments of the invention, the first mixture comprises the cell-binding agent having linkers stably and unstably bound thereto and one or more impurities (e.g., reactants and other by-products). A linker is "stably" bound to the cell-binding agent when the covalent bond between the linker and the cell-binding agent is not substantially weakened or severed under normal storage conditions over a period of time, which could range from a few months to a few years. In contrast, a linker is "unstably" bound to the cell-binding agent when the covalent bond between the linker and the cell-binding agent is substantially weakened or severed under normal storage conditions over a period of time, which could range from a few months to a few years.

The modification reaction preferably is performed at a pH of about 4 to about pH 9 (e.g., a pH of about 4.5 to about 8.5, about 5 to about 8, about 5.5 to about 7.5, about 6 to about 7, about 6 to about 8, about 6 to about 9, or about 6.5 to about 7.5). In some embodiments, the modification reaction is performed at a pH of about 6 to about 8 (e.g., a pH of about 6, about 6.5, about 7, about 7.5, or about 8).

In one embodiment, the modification reaction is performed at a pH of about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9. In another embodiment, the modification reaction is performed at a pH of about 7.5 to about 9, about 7.5 to about 8.5, about 7.5 to about 8, about 7.8 to about 9, about 7.8 to about 8.5, about 7.8 to about 8, about 8 to about 9, about 8 to about 8.5, or about 8.5 to about 9. In another embodiment the modification reaction is performed at a pH of about 7.8 (e.g., a pH of 7.6 to 8.0 or a pH of 7.7 to 7.9). In another embodiment, the modification reaction is performed at a pH of about 8 (e.g., a pH of 7.8 to 8.2 or a pH of 7.9 to 8.1).

In another embodiment, the modification reaction is performed at a pH that is greater than 7.5 (e.g., a pH of 7.6 to about 9, 7.7 to about 9, 7.8 to about 9, 7.9 to about 9, 7.6 to about 8.5, 7.6 to about 8, 7.7 to about 8.5, 7.7 to about 8, about 7.8 to about 8.4, about 7.8 to about 8.2, about 8 to about 9, or about 8 to about 8.5). For example, the inventive process comprises contacting a cell-binding agent with a bifunctional crosslinking reagent in a solution having a pH of 7.6, 7.7, 7.8, 7.9, 8, 8.1, 8.2, 8.3, 8.4, 8.5, 8.6, 8.7, 8.8, 8.9, or 9.

In one embodiment of the invention, purification of the modified cell-binding agent from impurities produced during the modification reaction (e.g., reactants and by-products) is carried out by subjecting the mixture produced by the modification reaction (i.e., the first mixture) to a purification process. In this regard, the first mixture can be purified using tangential flow filtration (TFF), e.g., a membrane-based tangential flow filtration process, non-adsorptive chromatography, adsorptive chromatography, adsorptive filtration, or selective precipitation, or any other suitable purification process, as well as combinations thereof. This first purification step provides a purified first mixture, i.e., an increased concentration of the cell-binding agents having linkers bound thereto and a decreased amount of unbound bifunctional crosslinking reagent, as compared to the first mixture prior to purification in accordance with the invention. Preferably, the first mixture is purified using tangential flow filtration or adsorptive chromatography (e.g., ion exchange chromatography, such as ceramic hydroxyapatite).

After purification of the first mixture to obtain a purified first mixture of cell-binding agents having linkers bound thereto, a cytotoxic agent is conjugated to the cell-binding agents having linkers bound thereto in the first purified mixture by reacting the cell-binding agents having linkers bound thereto with a cytotoxic agent in a solution having a pH from about 4 to about 9 to form a second mixture, wherein a second mixture comprising the cell-binding agent chemically coupled through the linker to the cytotoxic agent and one or more impurities (e.g., free cytotoxic agent and reaction by-products) is produced.

Optionally, purification of the modified cell-binding agent may be omitted. Thus, in one embodiment of the invention, the first mixture comprising the cell-binding agent having linkers bound thereto, as well as reactants and other by-products, is not subjected to a purification process. In such a situation, the cytotoxic agent may be added simultaneously with the crosslinking reagent or at some later point, e.g., 1, 2, 3, or more hours after addition of the crosslinking reagent to the cell-binding agent. The modified cell-binding agent is conjugated to a cytotoxic agent (e.g., a maytansinoid) by reacting the modified cell-binding agent with the cytotoxic agent in a solution having a pH from about 4 to about 9, wherein the conjugation step results in formation of a mixture of stable cell-binding agent-cytotoxic agent conjugates, non-stable cell-binding agent-cytotoxic agent conjugates, non-conjugated cytotoxic agent (i.e., "free" cytotoxic agent), reactants, and by-products.

The conjugation reaction preferably is performed at a pH of about 4 to about pH 9 (e.g., a pH of about 4.5 to about 8.5, about 5 to about 8, about 5.5 to about 7.5, about 6.0 to about 7, or about 6.5 to about 7.5). In some embodiments, the conjugation reaction is performed at a pH of about 6 to about 6.5 (e.g., a pH of 5.5 to 7, a pH of 5.7 to 6.8, a pH of 5.8 to 6.7, a pH of 5.9 to 6.6, or a pH of 6 to 6.5), a pH of about 6 or below (e.g., a pH of about 4 to 6, about 4 to about 5.5, about 5 to 6) or at a pH of about 6.5 or greater (e.g., a pH of 6.5 to about 9, about 6.5 to about 7, about 7 to about 9, about 7.5 to about 9, or 6.5 to about 8). In one embodiment, the conjugation reaction is performed at a pH of about 4 to a pH less than 6 or at a pH of greater than 6.5 to 9. When the conjugation step is performed at a pH of about 6.5 or greater, some sulfhydryl-containing cytotoxic agents may be prone to dimerize by disulfide-bond formation. In one embodiment, removal of trace metals and/or oxygen from the reaction mixture, as well as optional addition of antioxidants or the use of linkers with more reactive leaving groups, or addition of cytotoxic agent in more than one aliquot, may be required to allow for efficient reaction in such a situation.

Following the conjugation step, the mixture comprising the cell-binding agent cytotoxic agent conjugate and one or more impurities is subjected to a purification step. In this regard, the conjugation mixture can be purified using tangential flow filtration (TFF), e.g., a membrane-based tangential flow filtration process, non-adsorptive chromatography, adsorptive chromatography, adsorptive filtration, or selective precipitation, or any other suitable purification process, as well as combinations thereof. One of ordinary skill in the art will appreciate that purification after the conjugation step enables the isolation of a purified conjugate comprising the cell-binding agent chemically coupled to the cytotoxic agent, wherein the conjugate has a reduced amount of impurities as compared to the conjugate prior to the purification step. In one embodiment, the mixture comprising the cell-binding agent cytotoxic agent conjugate and one or more impurities is subjected to a PVDF membrane after the conjugation step and prior to the purification step in order to remove at least a portion of the impurities from the mixture prior to purification. In another embodiment, the mixture comprising the cell-binding agent cytotoxic agent conjugate and one or more impurities is subjected to a PVDF membrane after the purification step in order to remove at least a portion of the impurities remaining in the mixture after purification.

Thus, in one embodiment, the invention provides a process for preparing a conjugate comprising a cell-binding agent chemically coupled to a cytotoxic agent, which process comprises a first purification step after the modification step and a second purification step after the conjugation step, wherein the process comprises subjecting the mixture comprising a cell-binding agent cytotoxic agent conjugate and one or more impurities to a PVDF membrane either before or after the second purification step to remove at least a portion of the impurities from the mixture. In one embodiment, the invention provides a process for preparing a purified cell-binding agent cytotoxic agent conjugate comprising contacting a cell-binding agent with a bifunctional crosslinking reagent to covalently attach a linker to the cell-binding agent and thereby prepare a first mixture comprising cell-binding agents having linkers bound thereto, (b) subjecting the first mixture to tangential flow filtration, selective precipitation, non-adsorptive chromatography, adsorptive filtration, adsorptive chromatography, or a combination thereof and thereby prepare a purified first mixture of cell-binding agents having linkers bound thereto, (c) conjugating a cytotoxic agent to the cell-binding agents having linkers bound thereto in the purified first mixture by reacting the cell-binding agents having linkers bound thereto with a cytotoxic agent in a solution having a pH of about 4 to about 9 to prepare a second mixture comprising the cell-binding agent-cytotoxic agent conjugate comprising the cell-binding agent chemically coupled to the cytotoxic agent through the linker and one or more impurities, (d) subjecting the second mixture to a polyvinyl difluoride (PVDF) membrane to remove at least a portion of the impurities, thereby providing a purified second mixture of the cell-binding agent cytotoxic agent conjugate; and (e) subjecting the purified second mixture after step (d) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture.

Any purification method described herein can be used in the inventive process. In one embodiment of the invention, tangential flow filtration (TFF, also known as cross flow filtration, ultrafiltration and diafiltration) and/or adsorptive chromatography resins are utilized in the purification steps. For example, the inventive process can comprise a first purification step using TFF after the modification step and a second purification step using TFF after the conjugation step. Alternatively, the inventive process can comprise a first purification step using adsorptive chromatography after the modification step and a second purification step using adsorptive chromatography after the conjugation step. The inventive process also can comprise a first purification step using adsorptive chromatography after the modification step and a second purification step using TFF after the conjugation step or a first purification step using TFF after the modification step and a second purification step using adsorptive chromatography after the conjugation step.

In one embodiment of the invention, non-adsorptive chromatography is utilized as the purification step. For example, the inventive process can comprise a first purification step using non-adsorptive chromatography after the modification step and a second purification step using non-adsorptive chromatography after the conjugation step.

In another embodiment, the invention provides a process for preparing a conjugate comprising a cell-binding agent chemically coupled to a cytotoxic agent, wherein the first mixture comprising cell-binding agents having linkers bound thereto is not subjected to purification following the modification reaction and prior to the conjugation reaction, and wherein the process comprises subjecting the mixture comprising a cell-binding agent cytotoxic agent conjugate and one or more impurities to a PVDF membrane. When purification of the modified cell-binding agent is omitted, the invention provides a process for preparing a conjugate comprising a cell-binding agent chemically coupled to a cytotoxic agent, which process comprises a modification step, a conjugation step, and a first purification step after the conjugation step, wherein the process comprises subjecting the mixture comprising a cell-binding agent cytotoxic agent conjugate and one or more impurities to a PVDF membrane either before or after the first purification step to remove at least a portion of the impurities from the mixture. In one embodiment, the invention provides process for preparing a purified cell-binding agent cytotoxic agent conjugate comprising contacting a cell-binding agent with a bifunctional crosslinking reagent to covalently attach a linker to the cell-binding agent and thereby prepare a first mixture comprising cell-binding agents having linkers bound thereto, (b) conjugating a cytotoxic agent to the cell-binding agents having linkers bound thereto in the first mixture by reacting the cell-binding agents having linkers bound thereto with a cytotoxic agent to prepare a second mixture comprising the cell-binding agent-cytotoxic agent conjugate comprising the cell-binding agent chemically coupled through the linker to the cytotoxic agent and one or more impurities, (c) subjecting the second mixture to a polyvinyl difluoride (PVDF) membrane to remove at least a portion of the impurities, thereby providing a purified second mixture of the cell-binding agent cytotoxic agent conjugate; and (d) subjecting the purified second mixture after step (c) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture, and wherein the first mixture comprising the cell-binding agent having linkers bound thereto (as well as reactants and other by-products) prepared in step (a) is not subjected to a purification process prior to step (b). Any purification method described herein can be used as the purification step following the conjugation reaction. In a preferred embodiment, tangential flow filtration, adsorptive chromatography, or non-adsorptive chromatography is utilized as the purification step following the conjugation reaction.

In one embodiment, the invention provides a process for preparing a conjugate comprising a cell-binding agent chemically coupled to a cytotoxic agent, wherein the process comprises conjugating a pre-formed cytotoxic-agent-linker compound to a cell-binding agent, as described in U.S. Pat. No. 6,441,163 and U.S. Patent Application Publication Nos. 2011/0003969 and 2008/0145374, followed by a purification step, and wherein the process comprises subjecting the mixture comprising a cell-binding agent cytotoxic agent conjugate and one or more impurities to a PVDF membrane either before or after the purification step. Any purification method described herein can be used in the inventive process. In a preferred embodiment, tangential flow filtration, adsorptive chromatography, or non-adsorptive chromatography is utilized as the purification step.

In one embodiment, the cytotoxic agent-linker compound is prepared by contacting a cytotoxic agent with a bifunctional crosslinking reagent comprising a linker to covalently attach the cytotoxic agent to the linker. The cytotoxic agent-linker compound optionally is subjected to purification before contacting cytotoxic agent-linker compound with the cell-binding agent.

In one embodiment of the invention, the inventive process described herein (e.g., the one-step process) comprises two separate purification steps following the conjugation step. When the inventive process comprises two separate purification steps following the conjugation step, the mixture comprising a cell-binding agent cytotoxic agent conjugate and one or more impurities can be subjected to a PVDF membrane before either or both of the purification steps, or following the purification steps to remove at least a portion of the impurities from the mixture. Any purification method described herein can be used as the purification steps following the conjugation reaction. In a preferred embodiment, tangential flow filtration, adsorptive chromatography, non-adsorptive chromatography, or a combination thereof are utilized as the purification steps following the conjugation reaction.

Any suitable TFF systems may be utilized for purification, including a PELLICON type system (Millipore, Billerica, Mass.), a SARTOCON cassette system (Sartorius AG, Edgewood, N.Y.), and a CENTRASETTE type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA ULTROGEL hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP HYPERCEL resin (Pall Corp., East Hills, N.Y.). Examples of suitable HIC resins include BUTYL-SEPHAROSE, HEXYL-SEPHAROSE, PHENYL-SEPHAROSE, AND OCTYL-SEPHAROSE resins (all from GE Healthcare, Piscataway, N.J.), as well as MACRO-PREP Methyl and MACRO-PREP t-Butyl resins (Biorad Laboratories, Hercules, Calif.). Examples of suitable ion exchange resins include SP-SEPHAROSE, CM-SEPHAROSE, AND Q-SEPHAROSE resins (all from GE Healthcare, Piscataway, N.J.), and UNOSPHERE S resin (Bio-Rad Laboratories, Hercules, Calif.). Examples of suitable mixed mode ion exchangers include BAKERBOND ABX (stylized as "ABx") resin (JT Baker, Phillipsburg N.J.). Examples of suitable IMAC resins include CHELATING SEPHAROSE resin (GE Healthcare, Piscataway, N.J.) and PROFINITY IMAC resin (Bio-Rad Laboratories, Hercules, Calif.). Examples of suitable dye ligand resins include BLUE SEPHAROSE resin (GE Healthcare, Piscataway, N.J.) and AFFI-GEL blue resin (Bio-Rad Laboratories, Hercules, Calif.). Examples of suitable affinity resins include PROTEIN A SEPHAROSE resin (e.g., MABSELECT media, GE Healthcare, Piscataway, N.J.), where the cell-binding agent is an antibody, and lectin affinity resins, e.g. LENTIL LECTIN SEPHAROSE resin (GE Healthcare, Piscataway, N.J.), where the cell-binding agent bears appropriate lectin binding sites. Alternatively an antibody specific to the cell-binding agent may be used. Such an antibody can be immobilized to, for instance, SEPHAROSE 4 FAST FLOW resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment of the invention, the process described herein further comprises subjecting the mixture to an ion exchange chromatography membrane to remove at least a portion of the impurities from the mixture. The ion exchange chromatography membrane can be an anion exchange membrane, such as a Q membrane, or a cation exchange membrane, such as an S membrane. In one embodiment, the ion exchange chromatography membrane is an endotoxin removal exchange membrane. In a preferred embodiment, the ion exchange chromatography membrane is an anion exchange membrane (e.g., a Q membrane).

An anion exchange membrane is a positively charged microporous membrane. In one embodiment, the positively charged anion exchange moiety is quaternary ammonium group. In one embodiment, the positively charged microporous membrane comprises a porous substrate and a cross-linked coating having pendant cationic groups (see for example, those described in U.S. Pat. Nos. 6,780,327, 6,851,561, 7,094,347, 7,223,341, 7,396,465). In one embodiment, the porous substrate is hydrophilic (e.g., polyethersulfone or cross-linked cellulose matrix). In another embodiment, the cationic group is quaternary ammonium group. In another embodiment, the anion exchange membrane is a positively charged microporous membrane comprising a porous polyethersulfone substrate and a cross-linked coating having pendant quaternary ammonium groups.

In one embodiment, the mixture is subjected to a PVDF membrane prior to subjecting the mixture to an ion exchange chromatography membrane (e.g., a Q membrane or an S membrane). In another embodiment, the mixture is subjected to an ion exchange chromatography membrane prior to subjecting the mixture to a PVDF membrane. In yet another embodiment, the mixture is subject to an ion exchange chromatography membrane before and after subjecting the mixture to a PVDF membrane. In another embodiment, the mixture is subjected to a PVDF membrane before and after subjection the mixture to an ion exchange chromatography membrane.

The inventive process comprises performing the reactions described herein (e.g., the modification reaction, the conjugation reaction, or the one-step reaction) at any suitable temperature known in the art. For example, the reaction can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the reaction occurs at a temperature of about 16° C. to about 24° C. (e.g., about 16° C., about 17° C., about 18° C., about 19° C., about 20° C., about 21° C., about 22° C., about 23° C., about 24° C., or about 25° C.).

In one embodiment, the inventive process described herein further comprises a quenching step to quench any unreacted cytotoxic agent and/or unreacted bifunctional crosslinking reagent. The quenching step is performed prior to purification of the cell-binding agent cytotoxic agent. Alternatively, the quenching step is performed after purification of the cell-biding agent cytotoxic agent. In one embodiment, the inventive process comprises (a) contacting a cell-binding agent with a cytotoxic agent to form a mixture comprising the cell-binding agent and the cytotoxic agent and then contacting the mixture comprising the cell-binding agent and the cytotoxic agent with a bifunctional crosslinking reagent comprising a linker, in a solution having a pH of about 4 to about 9 to provide a mixture comprising the cell-binding agent cytotoxic agent conjugate, wherein the cell-binding agent is chemically coupled through the linker to the cytotoxic agent, and impurities (e.g., free cytotoxic agent and reaction by-products), (b) subjecting the mixture comprising the cell-binding agent cytotoxic agent conjugate and one or more impurities to a PVDF membrane, (c) quenching the mixture after step (b) to quench any unreacted cytotoxic agent and/or unreacted bifunctional crosslinking reagent, (d) subjecting the quenched mixture to a PVDF membrane, (e) optionally holding the mixture, (f) optionally subjecting the mixture to a PVDF membrane, and (g) purifying the mixture to provide a purified cell-binding agent cytotoxic agent conjugate. In another embodiment, the inventive process comprises (a) contacting a cell-binding agent with a cytotoxic agent to form a mixture comprising the cell-binding agent and the cytotoxic agent and then contacting the mixture comprising the cell-binding agent and the cytotoxic agent with a bifunctional crosslinking reagent comprising a linker, in a solution having a pH of about 4 to about 9 to provide a mixture comprising the cell-binding agent cytotoxic agent conjugate, wherein the cell-binding agent is chemically coupled through the linker to the cytotoxic agent, and impurities (e.g., free cytotoxic agent and reaction by-products), (b) subjecting the mixture comprising the cell-binding agent cytotoxic agent conjugate and one or more impurities to a PVDF membrane, (c) optionally quenching the mixture after step (b) to quench any unreacted cytotoxic agent and/or unreacted bifunctional crosslinking reagent, (d) optionally subjecting the quenched mixture to a PVDF membrane, (e) holding the mixture, (f) subjecting the mixture to a PVDF membrane, and (g) purifying the mixture to provide a purified cell-binding agent cytotoxic agent conjugate.

In one embodiment, the mixture is quenched by contacting the mixture with a quenching reagent. As used herein, the "quenching reagent" refers to a reagent that reacts with the free cytotoxic agent and/or the bifunctional crosslinking reagent.

In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the cytotoxic agent is quenched. The quenching step can help prevent the dimerization of the cytotoxic agent, particular the cytotoxic agent having an unreacted thiol group (such as DM1). The dimerized cytotoxic agent can be difficult to remove. The quenching step may also minimize any unwanted thiol-disulfide interchange reaction with the native antibody disulfide groups. Upon quenching with polar, charged thiol-quenching reagents (such as 4-maleimidobutyric acid or 3-maleimidopropionic acid), the excess, unreacted cytotoxic agent is converted into a polar, charged, water-soluble adduct that can be easily separated from the covalently-linked conjugate during the purification step. Quenching with non-polar and neutral thiol-quenching reagents can also be used.

In one embodiment, the mixture is quenched by contacting the mixture with a quenching reagent that reacts with the unreacted bifunctional crosslinking reagent. For example, nucleophiles can be added to the mixture in order to quench any unreacted bifunctional crosslinking reagent. The nucleophile preferably is an amino group containing nucleophile, such as lysine, taurine and hydroxylamine.

Alternatively, the mixture is quenched by lowering the pH of the mixture to about 5.0 (e.g., 4.8, 4.9, 5.0, 5.1 or 5.2). In another embodiment, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one embodiment, the mixture is quenched by lowering the pH of the mixture to 4.8.

In a preferred embodiment, the reaction (e.g., the modification step, the conjugation step, or the one-step reaction) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the cell-binding agent and the cytotoxic agent is contacted with the bifunctional crosslinking reagent.

The inventive process may optionally include the addition of sucrose to the reaction step (e.g., the modification step, the conjugation step, or the one-step reaction) to increase solubility and recovery of the cell-binding agent-cytotoxic agent conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and combinations thereof.

In one embodiment, the inventive process further comprises one or more (e.g., one, two, or three) holding steps to release the unstably bound linkers from the cell-binding agent. The holding step comprises holding the mixture after modification of the cell-binding agent with a bifunctional crosslinking reagent, after conjugation of a cytotoxic agent to the cell-binding agents having linkers bound thereto, and/or after a purification step. When the holding step comprises holding the mixture after conjugation of a cytotoxic agent to the cell-binding agents having linkers bound thereto and/or after a purification step following the conjugation step, the mixture can be subjected to a PVDF membrane before or after the holding step, or both. In one embodiment, the process comprises subjecting a mixture comprising a cell-binding agent cytotoxic agent conjugate and one or more impurities to a holding step after the conjugation step, wherein the mixture is subjected to a PVDF membrane after the holding step and prior to the purification step. In another embodiment, the process comprises subjecting a mixture comprising a cell-binding agent cytotoxic agent conjugate and one or more impurities to a holding step after the conjugation step, wherein the mixture is subjected to a purification step after the holding step, followed by subjecting the mixture to a PVDF membrane. The mixture optionally may be subjected to a second holding step prior to subjecting the mixture to the PVDF membrane.

The holding step comprises maintaining the solution at a suitable temperature (e.g., about 2° C. to about 37° C.) for a suitable period of time (e.g., about 1 hour to about 1 week) to release the unstably bound linkers from the cell-binding agent while not substantially releasing the stably bound linkers from the cell-binding agent. In one embodiment, the holding step comprises maintaining the solution at a low temperature (e.g., about 2° C. to about 10° C. or about 4° C.), at room temperature (e.g., about 20° C. to about 30° C. or about 20° C. to about 25° C.), or at an elevated temperature (e.g., about 30° C. to about 37° C.).

The duration of the holding step depends on the temperature at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 5 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), for about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to 1 day.

The pH value for the holding step preferably is about 4 to about 9 (e.g., about 4.5 to about 8.5 or about 5 to about 8). In one embodiment, the pH values for the holding step range from about 5 to about 7.5 (e.g., about 5.5 to about 7.5, about 6 to about 7.5, about 6.5 to about 7.5, about 7 to about 7.5, about 5 to about 7, about 5 to about 6.5, about 5 to about 5.5, about 5.5 to about 7, about 6 to about 6.5, or about 6 to about 7). For example, pH values for the holding step can be about 4, about 4.5, about 5, about 5.5, about 6, about 6.5, about 7, about 7.5, about 8, about 8.5, or about 9.

The holding step can be performed before or after the cell-binding agent is conjugated to the cytotoxic agent. In one embodiment, the holding step is performed directly after the modification of the cell-binding agent with the bifunctional crosslinking reagent. For example, the inventive process comprises a holding step after modification of the cell-binding agent with a bifunctional crosslinking reagent and before conjugation. After modification of the cell-binding agent, a purification step may be performed before the hold step and/or after the hold step, but prior to the conjugation step. In another embodiment, the holding step is performed directly after conjugation of the cytotoxic agent to the cell-binding agent having linkers bound thereto and prior to purification step. In another embodiment, the holding step is performed after the conjugation and purification steps and followed by an additional purification step.

In specific embodiments, the holding step can comprise incubating the mixture at a pH of about 5-7.5 or about 6.5-7.5 for about 1 hour to about 1 week at about 2° C. to about room temperature.

In one embodiment, the invention provides a process for preparing a cell-binding agent-cytotoxic agent conjugate, which process comprises the addition of exogenous NHS. "Exogenous NHS," as used herein, refers to NHS that is added during the process from an external source, and does not refer to NHS that is generated during the modification reaction as a result of hydrolysis/aminolysis of the bifunctional linker.

In one embodiment, the invention provides a process for preparing a cell-binding agent-cytotoxic agent conjugate, which process comprises the addition of about 0.1 mM to about 300 mM exogenous NHS. For example, the inventive process comprises the addition of about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.3 mM, about 1.5 mM, about 1.7 mM, about 1.9 mM, about 2.0 mM, about 2.1 mM, about 2.3 mM, about 2.5 mM, about 2.7 mM, about 2.9 mM, about 3.0 mM, about 3.1 mM, about 3.3 mM, about 3.5 mM, about 3.7 mM, about 3.9 mM, about 4.0 mM, about 4.1 mM, about 4.3 mM, about 4.5 mM, about 4.7 mM, about 4.9 mM, about 5.0 mM, about 5.1 mM, about 5.3 mM, about 5.5 mM, about 5.7 mM, about 5.9 mM, about 6.0 mM, about 6.1 mM, about 6.3 mM, about 6.5 mM, about 6.7 mM, about 6.9 mM, about 7.0 mM, about 7.1 mM, about 7.3 mM, about 7.5 mM, about 7.7 mM, about 7.9 mM, about 8.0 mM, about 8.1 mM, about 8.3 mM, about 8.5 mM, about 8.7 mM, about 8.9 mM, about 9.0 mM, about 9.1 mM, about 9.3 mM, about 9.5 mM, about 9.7 mM, about 9.9 mM, about 10 mM, about 11 mM, about 12 mM, about 13 mM, about 14 mM, about 15 mM, about 16 mM, about 17 mM, about 18 mM, about 19 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, or about 300 mM exogenous NHS. In one embodiment, the inventive process comprises the addition of about 0.1 mM to about 5 mM, about 0.1 mM to about 10 mM, about 1.0 mM to about 5 mM, about 1.0 mM to about 10 mM, about 5.0 mM to about 10 mM, about 10 mM to about 20 mM, about 20 mM to about 30 mM, about 30 mM to about 40 mM, about 40 mM to about 50 mM, about 50 mM to about 60 mM, about 60 mM to about 70 mM, about 70 mM to about 80 mM, about 80 mM to about 90 mM, about 90 mM to about 100 mM, about 100 mM to about 110 mM, about 110 mM to about 120 mM, about 120 mM to about 130 mM, about 130 mM to about 140 mM, about 140 mM to about 150 mM, about 150 mM to about 160 mM, about 160 mM to about 170 mM, about 170 mM to about 180 mM, about 180 mM to about 190 mM, about 190 mM to about 200 mM, about 200 mM to about 220 mM, about 220 mM to about 240 mM, about 240 mM to about 260 mM, about 260 mM to about 280 mM, or about 280 mM to about 300 mM exogenous NHS. In another embodiment, the inventive process comprises the addition of about 10 mM to about 200 mM, about 20 to about 150 mM, about 50 to about 150 mM, or about 20 to about 100 mM exogenous NHS.

In some embodiments, the inventive process comprises the addition of a molar ratio of exogenous NHS with respect to the amount of NHS generated during the modification reaction as a result of hydrolysis/aminolysis of the bifunctional linker. One of ordinary skill in the art can determine the amount of NHS generated during a particular modification as the amount of NHS generated is essentially the same as the amount of the bifunctional linker used. The skilled person can then add a molar ratio of exogenous NHS to the reaction mixture with respect to the amount of NHS generated during the modification reaction. In one embodiment, about 2 to about 200 fold exogenous NHS is added with respect to the amount of NHS generated during the modification reaction. For example, the inventive process comprises adding about 2, about 5, about 10, about 15, about 20, about 25, about 50, about 100, or about 200 fold exogenous NHS with respect to the amount of NHS generated during the modification reaction.

In some embodiments, the inventive process comprises the addition of a molar ratio of exogenous NHS with respect to the amount of the bifunctional linker. In one embodiment, the molar ratio of the exogenous NHS to the bifunctional crosslinking agent is about 0.5 to about 1000 (e.g., about 1 to about 900, about 5 to about 750, about 50 to about 500, about 100 to about 500, about 0.5 to about 500, or about 100 to about 1000. For example, the inventive process comprises about 0.5, about 1, about 2, about 5, about 10, about 15, about 20, about 25, about 50, about 100, about 200, about 300, about 400, about 500, about 600, about 700, about 800, about 900, or about 1000 fold NHS with respect to the amount of the bifunctional linker.

The inventive process comprises the addition of exogenous NHS at any point during a process preparing a cell-binding agent-cytotoxic agent conjugate. For example, the inventive process comprises the addition of exogenous NHS to the modification step (i.e., the step in which a cell-binding agent is reacted with a bifunctional linker), to the conjugation step (i.e., the step in which a modified cell-binding agent is reacted with a cytotoxic agent), to a purification step, or to a holding step between any of the foregoing steps. In one embodiment, the inventive process comprises the addition of exogenous NHS to the modification step (i.e., NHS is added to the modification reaction), to a holding step between the modification step and a purification step, to a holding step between the modification step and the conjugation step, to a purification step, to the conjugation step, to a holding step between the conjugation step and a purification step, and/or to a holding step between two purification steps.

In one embodiment, the invention provides a process for preparing a cell-binding agent having a linker bound thereto, which process comprises contacting a cell-binding agent with a bifunctional crosslinking reagent in the presence of exogenous NHS to covalently attach a linker to the cell-binding agent and thereby prepare a mixture comprising cell-binding agents having linkers bound thereto.

The invention provides a process for preparing compositions of stable conjugates comprising a cell-binding agent chemically coupled to a cytotoxic agent, wherein the compositions are substantially free of unstable conjugates. In this respect, the invention provides a process for preparing cell-binding agent-cytotoxic agent conjugate of substantially high purity and stability. Such compositions can be used for treating diseases because of the high purity and stability of the conjugates. Compositions comprising a cell-binding agent, such as an antibody, chemically coupled to a cytotoxic agent, such as a maytansinoid, are described in, for example, U.S. Pat. No. 7,374,762. In one aspect of the invention, a cell-binding agent-cytotoxic agent conjugate of substantially high purity has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation or purified conjugate is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free cytotoxic agent level in the conjugate preparation or purified conjugate is less than about 5%, less than about 3%, less than about 2% (e.g., less than or equal to about 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (relative to total cytotoxic agent), (f) cytotoxic dimer species level in the conjugate preparation or purified conjugate is less than about 5%, less than about 3%, less than about 2% (e.g., less than or equal to about 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (relative to total cytotoxic agent), and/or (e) no substantial increase in free cytotoxic agent level upon storage (e.g., after about 1 week, about 2 weeks, about 3 weeks, about 1 month, about 2 months, about 3 months, about 4 months, about 5 months, about 6 months, about 1 year, about 2 years, or about 5 years). "Substantial increase" in free cytotoxic agent level means that after certain storage time, the increase in the level of free cytotoxic agent is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the cell-binding agent that is covalently linked with the bifunctional crosslinking reagent, wherein the cell-binding agent is not covalently coupled to the cytotoxic agent through the linker of the bifunctional crosslinking reagent (i.e., the "unconjugated linker" can be represented by CBA-L, wherein CBA represents the cell-binding agent and L represents the bifunctional crosslinking reagent. In contrast, the cell-binding agent cytotoxic agent conjugate can be represented by CBA-L-D, wherein D represents the cytotoxic agent).

As used herein, the term "cytotoxic agent dimers" refers to dimers comprising free cytotoxic agent, wherein the cytotoxic agent is not chemically coupled to the cell-binding agent through the linker. In one embodiment, the cytotoxic agent dimers are chemically coupled to each other through a linker (i.e., the "cytotoxic agent dimers" can be represented by D-L-D, wherein D represents the cytotoxic agent and L represents the bifunctional crosslinking reagent. In contrast, the cell-binding agent cytotoxic agent conjugate can be represented by CBA-L-D, wherein CBA represents the cell-binding agent). In another embodiment, the cytotoxic agent dimers are not chemically coupled to each other through a linker (i.e., the "cytotoxic agent dimers" can be represented by D-D, wherein D represents the cytotoxic agent. In contrast, the cell-binding agent cytotoxic agent conjugate can be represented by CBA-L-D, wherein CBA represents the cell-binding agent and L represents the bifunctional crosslinking reagent). In one embodiment, some of the cytotoxic agent dimers are chemically coupled to each other through a linker and some of the cytotoxic agent dimers are not chemically coupled to each other through a linker (i.e., the "cytotoxic agent dimers" can be represented by D-L-D and D-D, wherein D represents the cytotoxic agent and L represents the bifunctional crosslinking reagent). In one embodiment, the cytotoxic agent dimers are DM1-DM1 dimer and DM1-MCC-DM1 dimer, when the linker is SMCC and the cytotoxic agent is DM1.

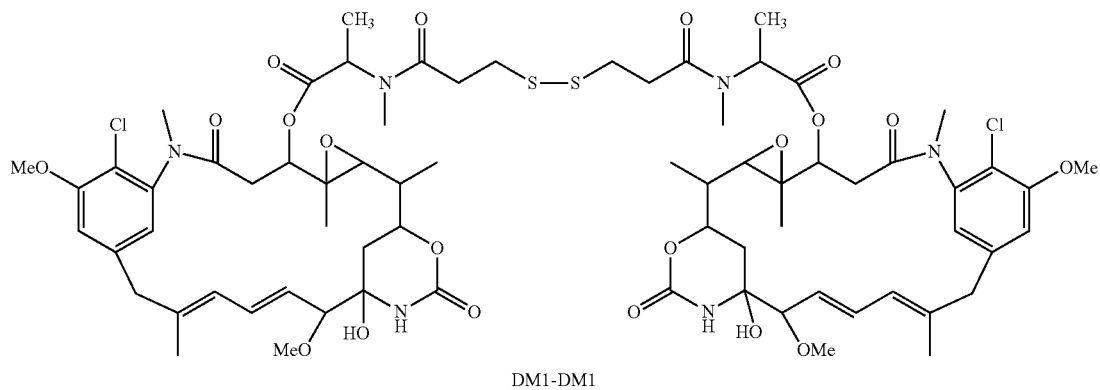

DM1-DM1

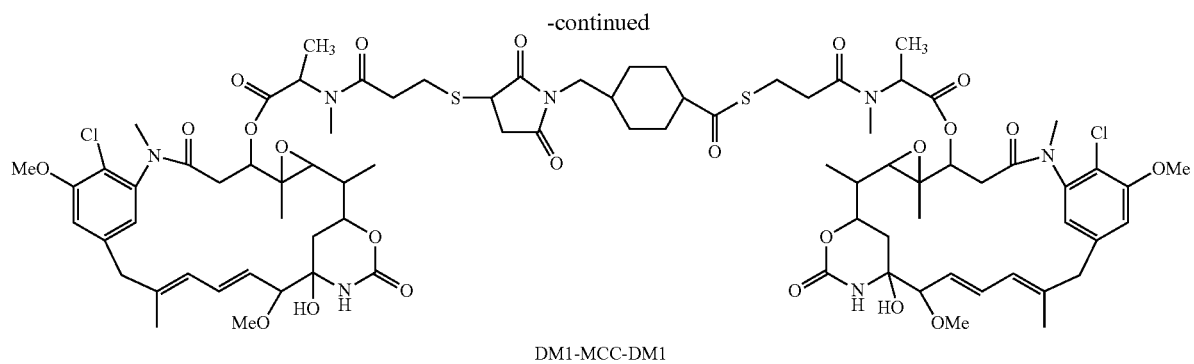

DM1-MCC-DM1

In another embodiment, the cytotoxic agent dimers are DM1-DM1 dimers and DM1-SPP-DM1 dimers, when the linker is SPP and the cytotoxic agent is DM1.

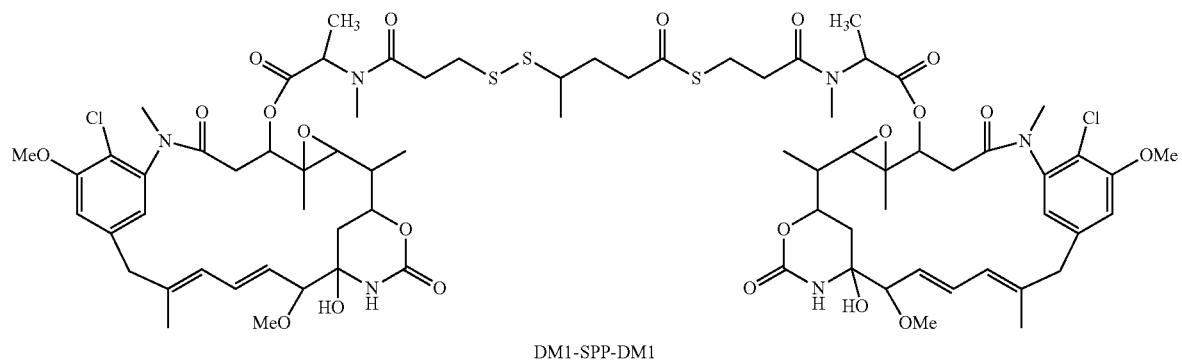 [SMILES: COc1cc2cc(c1Cl)N(C)C(=O)CC(OC(=O)C(C)N(C)C(=O)CCSSC(C)CCC(=O)SCCC(=O)N(C)C(C)C(=O)OC1CC(=O)N(C)c3cc(cc(OC)c3Cl)C/C(C)=C/C=C/C(OC)C3(O)CC(OC(=O)N3)C(C)C3OC13C)C1(C)OC1C(C)C1CC(O)(NC(=O)O1)C(OC)/C=C/C=C(\C)C2]

DM1-SPP-DM1

In another embodiment, the cytotoxic agent dimers are DM1-DM1 dimers and DM1-CX1-1-DM1 dimers, when the linker is CX1-1 and the cytotoxic agent is DM1.

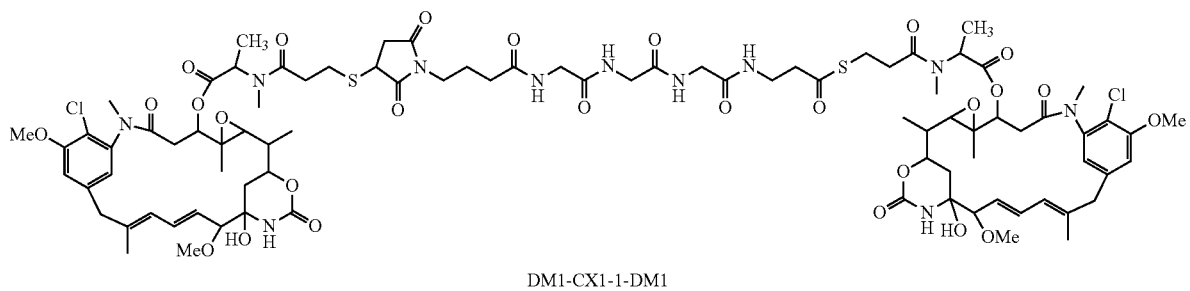 [SMILES: COc1cc2cc(c1Cl)N(C)C(=O)CC(OC(=O)C(C)N(C)C(=O)CCSC(=O)CCNC(=O)CNC(=O)CNC(=O)CNC(=O)CCCN1C(=O)CC(SCCC(=O)N(C)C(C)C(=O)OC3CC(=O)N(C)c4cc(cc(OC)c4Cl)C/C(C)=C/C=C/C(OC)C4(O)CC(OC(=O)N4)C(C)C4OC34C)C1=O)C1(C)OC1C(C)C1CC(O)(NC(=O)O1)C(OC)/C=C/C=C(\C)C2]

DM1-CX1-1-DM1

As used herein, the term "free cytotoxic agent" refers to any form of the cytotoxic agent that is not chemically coupled to the cell-binding agent through the linker (i.e., the "free cytotoxic agent" can include, but is not limited to, the cytotoxic agent alone represented by D, the cytotoxic agent coupled with the linker or linker derivatives (e.g. hydrolyzed derivatives) represented by D-L and cytotoxic agent dimers represented by D-D and D-L-D described above).

In one embodiment, the free cytotoxic agent includes DM1, MCC-DM1, hydro-SMCC-DM1, SMCC-DM1, DM1-SPP, DM1-TPA, DM1-DM1, DM1-MCC-DM1, and DM1-SPP-DM1.

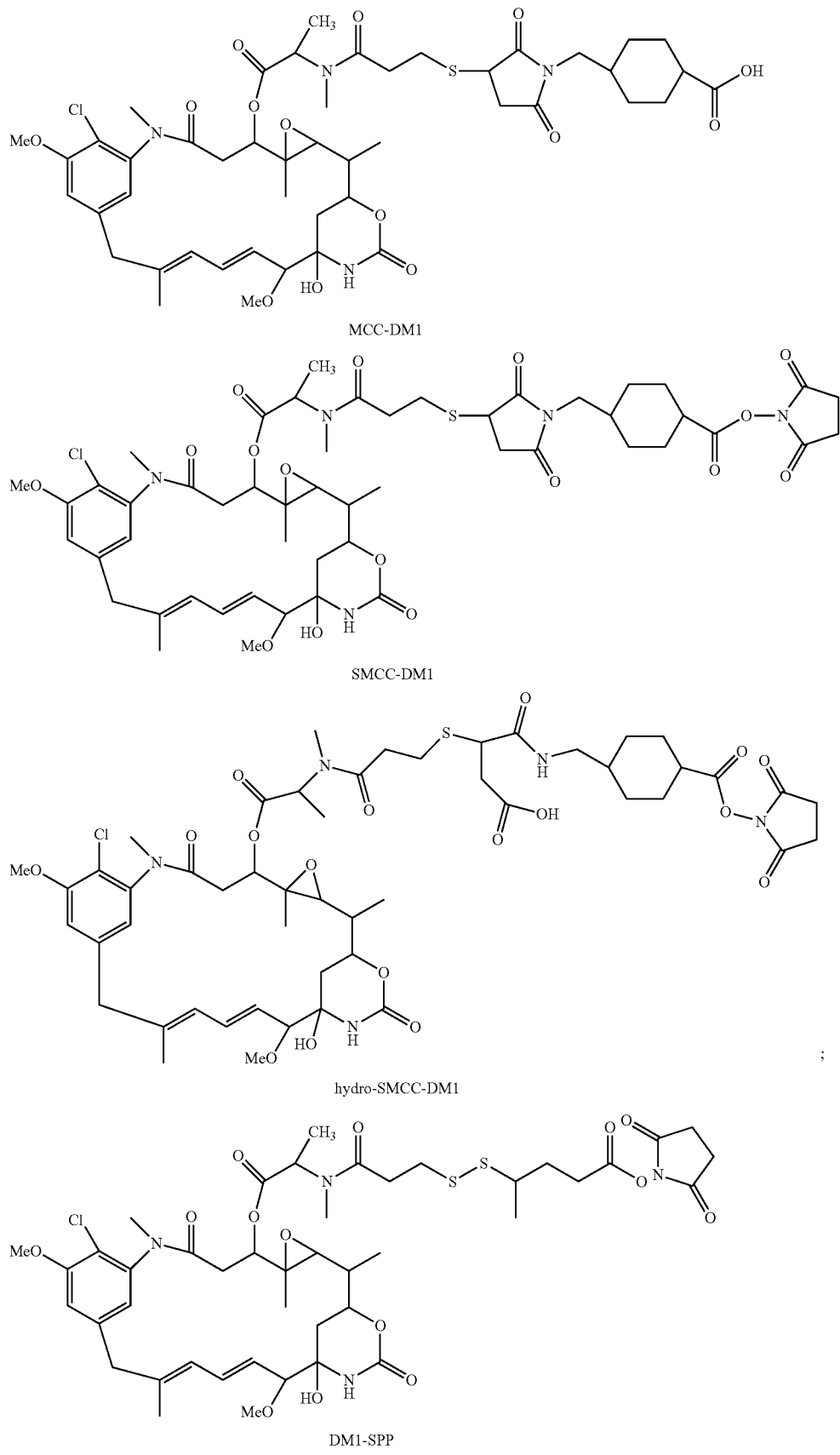

-continued

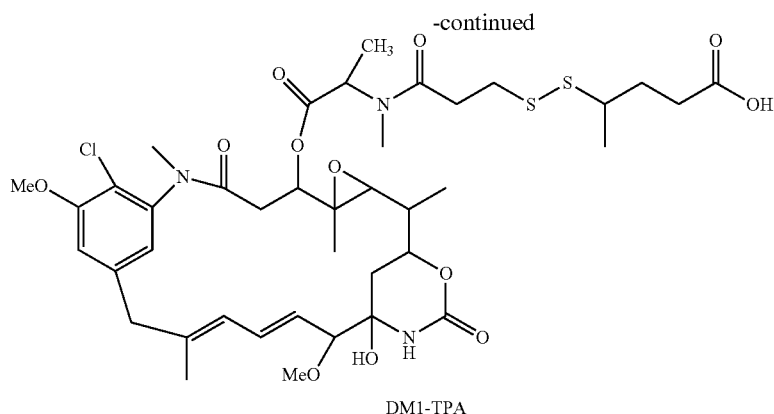

DM1-TPA

As used herein, the term "aggregates of the cell-binding agent cytotoxic agent conjugate" refers to two or more cell-binding agent cytotoxic agent conjugates covalently or noncovalently coupled to each other (e.g., two or more cell-binding agent cytotoxic agent conjugates covalently coupled through the linker).

In one embodiment, the average molar ratio of the cytotoxic agent to the cell-binding agent in the cell-binding agent cytotoxic agent conjugate is about 1 to about 10, about 2 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, about 4.5 to 5.5 (e.g., about 4.5, about 4.6, about 4.7, about 4.8, about 4.9, about 5.0, about 5.1, about 5.2, about 5.3, about 5.4, about 5.5).

The cell-binding agent can be any suitable agent that binds to a cell, typically and preferably an animal cell (e.g., a human cell). The cell-binding agent preferably is a peptide or a polypeptide or a glycotope. Suitable cell-binding agents include, for example, antibodies (e.g., monoclonal antibodies and fragments thereof), interferons (e.g., alpha, beta, gamma), lymphokines (e.g., interleukin 2 (IL-2), interleukin 3 (IL-3), interleukin 4 (IL-4), interleukin 6 (IL-6), hormones (e.g., insulin, TRH (thyrotropin releasing hormone), MSH (melanocyte-stimulating hormone), steroid hormones, such as androgens and estrogens), growth factors and colony-stimulating factors, such as epidermal growth factor (EGF), transforming growth factor alpha (TGF-alpha), fibroblast growth factor (FGF), vascular endothelial growth factor (VEGF), colony stimulating factors (CSFs), such as G-CSF, M-CSF and GM-CSF (Burgess, *Immunology Today* 5:155-158 (1984)), nutrient-transport molecules (e.g., transferrin), vitamins (e.g., folate) and any other agent or molecule that specifically binds a target molecule on the surface of a cell.

Where the cell-binding agent is an antibody, it binds to an antigen that is a polypeptide and may be a transmembrane molecule (e.g., receptor) or a ligand, such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor (FGF) such as aFGF and bFGF; fibroblast growth factor receptor such as FGFR24 and FGFR3, epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in U.S. Patent Application Publication No. 2008/0171040 or U.S. Patent Application Publication No. 2008/0305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, IGF1R, prostate antigens such as PCA3, PSA, PSGR, NGEP, PSMA, PSCA, TMEFF2, and STEAP1; LGR5, B7H4, and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents The term "antibody," as used herein, refers to any immunoglobulin, any immunoglobulin fragment, such as Fab, Fab', F(ab')$_2$, dsFv, sFv, minibodies, diabodies, tribodies, tetrabodies (Parham, *J. Immunol.* 131: 2895-2902 (1983); Spring et al. *J. Immunol.* 113: 470-478 (1974); Nisonoff et al. *Arch. Biochem. Biophys.* 89: 230-244 (1960), Kim et al., *Mol. Cancer Ther.,* 7: 2486-2497 (2008), Carter, *Nature Revs.,* 6: 343-357 (2006)), or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, *Eur. J. Immunol.,* 5: 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, *J. Immunol. Methods,* 74(2): 361-67 (1984), and Roder et al., *Methods Enzymol.,* 121: 140-67 (1986)), bacteriophage vector expression systems (see, e.g., Huse et al., *Science,* 246: 1275-81 (1989)), or phage display libraries comprising antibody fragments, such as Fab and scFv (single chain variable region) (see, e.g., U.S. Pat. Nos. 5,885,793 and 5,969,108, and International Patent Application Publications WO 92/01047 and WO 99/06587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-cytotoxic agent conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235: 959-973 (1994). While the antibody employed in the conjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')$_2$ fragment. Reduction of a F(ab')$_2$ fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, *J. Immunol.*, 131: 2895-2902 (1983), Spring et al., *J. Immunol.*, 113: 470-478 (1974), and Nisonoff et al., *Arch. Biochem. Biophys.*, 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., *Nature Struct. Biol.*, 3: 752, (1996)), or a shark antibody, such as, for example, a new antigen receptor (IgNAR) (see, e.g., Greenberg et al., *Nature*, 374: 168 (1995), and Stanfield et al., *Science*, 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., *Nature*, 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., *Leukemia Res.*, 8: 521 (1984)), and can be used to target cells that express CD33 (e.g., acute myelogenous leukemia (AML) cells). Similarly, the monoclonal antibody anti-B4 (also referred to as B4) is a murine IgG1 antibody that binds to the CD19 antigen on B cells (Nadler et al., *J. Immunol.*, 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the conjugate to target drugs to cells of neuroendocrine origin. The J5, MY9, and B4 antibodies preferably are resurfaced or humanized prior to their use as part of the conjugate. Resurfacing or humanization of antibodies is described in, for example, Roguska et al., *Proc. Natl. Acad. Sci. USA*, 91: 969-73 (1994). In one embodiment, the anti-B4 antibody is huB4. In another embodiment, the anti-B4 antibody comprises a heavy chain and a light chain, wherein the heavy chain has the following sequence

```
                                          (SEQ ID NO: 1)
QVQLVQPGAE VVKPGASVKL SCKTSGYTFT SNWMHWVKQA

PGQGLEWIGE IDPSDSYTNY NQNFQGKAKL TVDKSTSTAY

MEVSSLRSDD TAVYYCARGS NPYYYAMDYW GQGTSVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK
``` and the light chain has the following sequence

```
                                          (SEQ ID NO: 2)
EIVLTQSPAI MSASPGERVT MTCSASSGVN YMHWYQQKPG

TSPRRWIYDT SKLASGVPAR FSGSGSGTDY SLTISSMEPE

DAATYYCHQR GSYTFGGGTK LEIKRTVAAP SVFIFPPSDE
```

```
QLKSGTASVV CLLNNFYPRE AKVQWKVDNA LQSGNSQESV

TEQDSKDSTY SLSSTLTLSK ADYEKHKVYA CEVTHQGLSS

PVTKSFNRGE C.
```

In addition, the monoclonal antibody C242 binds to the CanAg antigen (see, e.g., U.S. Pat. No. 5,552,293), and can be used to target the conjugate to CanAg expressing tumors, such as colorectal, pancreatic, non-small cell lung, and gastric cancers. HuC242 is a humanized form of the monoclonal antibody C242 (see, e.g., U.S. Pat. No. 5,552,293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693,762) or resurfacing technology (see, e.g., U.S. Pat. No. 5,639,641). HuC242 can be used to target the conjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the conjugate. Anti-MUC1 antibodies include, for example, anti-HMFG-2 (see, e.g., Taylor-Papadimitriou et al., *Int. J. Cancer*, 28: 17-21 (1981)), hCTM01 (see, e.g., van Hof et al., *Cancer Res.*, 56: 5179-5185 (1996)), and DS6. Prostate cancer cells also can be targeted with the conjugate by using an anti-prostate-specific membrane antigen (PSMA) as the cell-binding agent, such as J591 (see, e.g., Liu et al., *Cancer Res.*, 57: 3629-3634 (1997)). Moreover, cancer cells that express the Her2 antigen, such as breast, prostate, and ovarian cancers, can be targeted with the conjugate by using anti-HER2 antibodies, e.g., trastuzumab, as the cell-binding agent. Cells that express epidermal growth factor receptor (EGFR) and variants thereof, such as the type III deletion mutant, EGFRvIII, can be targeted with the conjugate by using anti-EGFR antibodies. Anti-EGFR antibodies are described in International Patent Application Nos. PCT/US11/058385 and PCT/US11/058378. Anti-EGFRvIII antibodies are described in U.S. Pat. Nos. 7,736,644 and 7,628,986, and U.S. Patent Application Publications 2010/0111979; 2009/0240038; 2009/0175887; 2009/0156790; and 2009/0155282. Anti-IGF-IR antibodies that bind to insulin-like growth factor receptor, such as those described in U.S. Pat. No. 7,982,024, also can be used in the conjugate. Antibodies that bind to CD27L, Cripto, CD138, CD38, EphA2, integrins, CD37, folate, CD20, PSGR, NGEP, PSCA, TMEFF2, STEAP1, endoglin, and Her3 also can be used in the conjugate.

In one embodiment, the antibody is selected from the group consisting of huN901, anti-CD33 antibody (e.g., huMy9-6), huB4, huC242, an anti-HER2 antibody (e.g., trastuzumab), bivatuzumab, sibrotuzumab, rituximab, huDS6, anti-mesothelin antibodies described in International Patent Application Publication WO 2010/124797 (such as MF-T), anti-cripto antibodies described in U.S. Patent Application Publication 2010/0093980 (such as huB3F6), anti-CD138 antibodies described in U.S. Patent Application Publication 2007/0183971 (such as B-B4 or humanized B-B4 or nBT062), anti-EGFR antibodies described in International Patent Application Publications WO 2012/058592 and WO 2012/058588 (such as EGFR-7), anti-EGFRvIII antibodies described U.S. Pat. Nos. 7,736,644 and 7,628,986 and U.S. Patent Application Publications 2010/0111979, 2009/0240038, 2009/0175887, 2009/0156790 and 2009/0155282, humanized EphA2 antibodies described in International Patent Application Publications WO 2011/039721 and WO 2011/039724 (such as 2H11R35R74); anti-CD38 antibodies described in International Patent Application Publication WO 2008/047242 (such as hu38SB19), anti-folate receptor antibodies described in International Patent Application Publication WO 2011/106528, and U.S. Patent Application Publication 2012/0009181 (e.g., huMov19 version 1.0 or 1.6); anti-IGF1R antibodies described in U.S. Pat. Nos. 5,958,872, 6,596,743, and 7,982,024; anti-CD37 antibodies described in U.S. Patent Application Publication 2011/0256153 (e.g., huCD37-3 version 1.0); anti-integrin $\alpha_v\beta_6$ antibodies described in U.S. Patent Application Publication 2006/0127407 (e.g., CNTO95); and anti-Her3 antibodies described in International Patent Application Publication WO 2012/019024. In one embodiment of the invention, the antibody is not huN901, or CNTO95. In one embodiment, the anti-CD37 antibody is huCD37-3, wherein the antibody comprises a variable heavy chain and a variable light chain, wherein the variable heavy chain has the following sequence

```
                                           (SEQ ID NO: 3)
QVQVQESGPGLVAPSQTLSITCTVSGFSLTTSGVSWVRQPPGKGLEWLGV

IWGDGSTNYHPSLKSRLSIKKDHSKSQVFLKLNSLTAADTATYYCAKGGY

SLAHWGQGTLVTVSS
``` and the variable light chain has the following sequence

```
                                           (SEQ ID NO: 4)
DIQMTQSPSSLSVSVGERVTITCRASENIRSNLAWYQQKPGKSPKLLVNV

ATNLADGVPSRFSGSGSGTDYSLKINSLQPEDFGTYYCQHYWGTTWTF

GQGTKLEIKR.
```

While the cell-binding agent preferably is an antibody, the cell-binding agent also can be a non-antibody molecule. Suitable non-antibody molecules include, for example, interferons (e.g., alpha, beta, or gamma interferon), lymphokines (e.g., interleukin 2 (IL-2), IL-3, IL-4, or IL-6), hormones (e.g., insulin), growth factors (e.g., EGF, TGF-alpha, FGF, and VEGF), colony-stimulating factors (e.g., G-CSF, M-CSF, and GM-CSF (see, e.g., Burgess, *Immunology Today*, 5: 155-158 (1984)), somatostatin, and transferrin (see, e.g., O'Keefe et al., *J. Biol. Chem.*, 260: 932-937 (1985)). For example, GM-CSF, which binds to myeloid cells, can be used as a cell-binding agent to target acute myelogenous leukemia cells. In addition, IL-2, which binds to activated T-cells, can be used for prevention of transplant graft rejection, for therapy and prevention of graft-versus-host disease, and for treatment of acute T-cell leukemia. Epidermal growth factor (EGF) can be used to target squamous cancers such as lung cancer and head and neck cancer. Somatostatin can be used to target neuroblastoma cells and other tumor cell types.

The conjugate can comprise any suitable cytotoxic agent. A "cytotoxic agent," as used herein, refers to any compound that results in the death of a cell, induces cell death, or decreases cell viability. Suitable cytotoxic agents include, for example, maytansinoids and maytansinoid analogs, taxoids, CC-1065 and CC-1065 analogs, and dolastatin and dolastatin analogs. In a preferred embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl) +/–C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/–dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy$CH_2$OR) (U.S. Pat. No. 4,331,598), (3) C-14-hydroxymethyl or acyloxymethyl ($CH_2$OH or $CH_2$OAc) (U.S. Pat. No. 4,450,254) (prepared from *Nocardia*), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In a preferred embodiment of the invention, the conjugate utilizes the thiol-containing maytansinoid DM1, also known as $N^{2'}$-deacetyl-$N^{2'}$-(3-mercapto-1-oxopropyl)-maytansine, as the cytotoxic agent. The structure of DM1 is represented by formula (I):

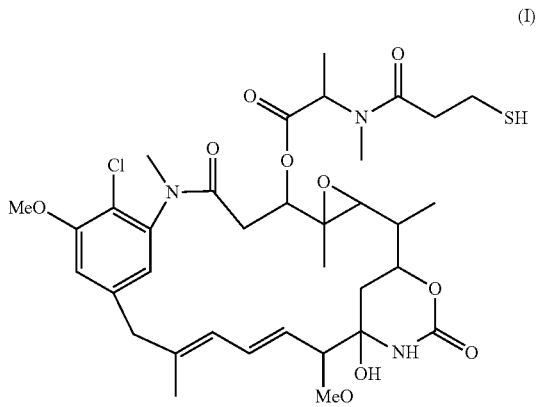 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

(I)

In another preferred embodiment of the invention, the conjugate utilizes the thiol-containing maytansinoid DM4, also known as $N^{2'}$-deacetyl-$N^{2'}$-(4-methyl-4-mercapto-1-oxopentyl)-maytansine, as the cytotoxic agent. The structure of DM4 is represented by formula (II):

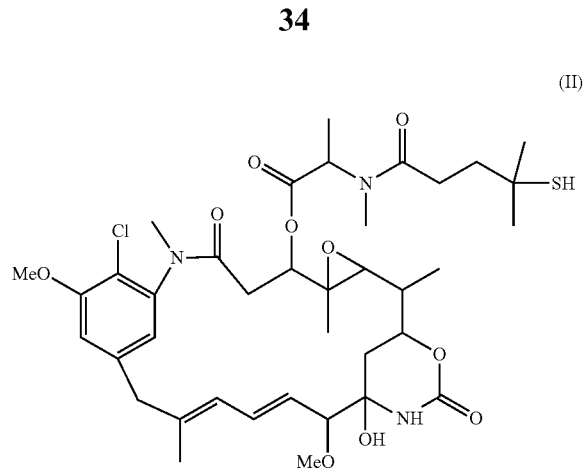

(II)

Other maytansines may be used in the context of the invention, including, for example, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansines for use in the context of the invention include compounds represented by formula (III):

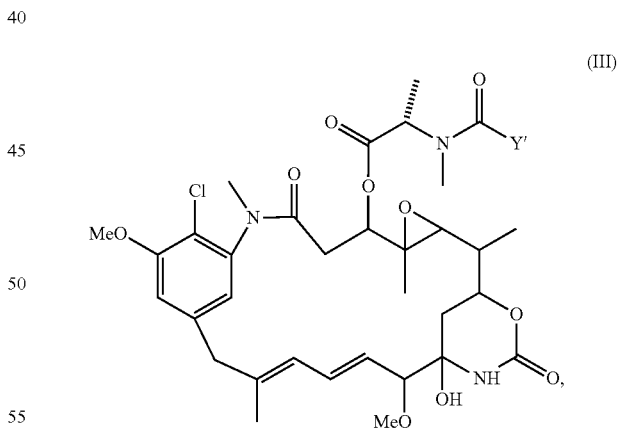

(III)

wherein Y' represents $(CR_7R_8)_l(CR_9=CR_{10})_p(C\equiv C)A_o(CR_5R_6)_mD_u(CR_{11}=CR_{12})_r(C\equiv C)_sB_t(CR_3R_4)_nCR_1R_2SZ$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein A, B, D are cycloalkyl or cycloalkenyl having 3-10 carbon atoms, simple or substituted aryl, or heterocyclic aromatic, or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic, or heterocycloalkyl radical, wherein l, m, n, o, p, q, r, s, and t are each independently zero or an integer from 1 to 5, provided that at least two of l, m, n, o, p, q, r, s and t are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic, or heterocycloalkyl radical.

Preferred embodiments of formula (III) include compounds of formula (III) wherein (a) $R_1$ is H, $R_2$ is methyl and Z is H, (b) $R_1$ and $R_2$ are methyl and Z is H, (c) $R_1$ is H, $R_2$ is methyl, and Z is —$SCH_3$, and (d) $R_1$ and $R_2$ are methyl, and Z is —$SCH_3$.

Such additional maytansines also include compounds represented by formula (IV-L), (IV-D), or (IV-D,L):

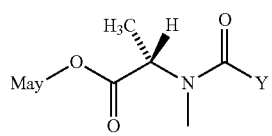

(IV-L)

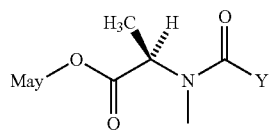

(IV-D)

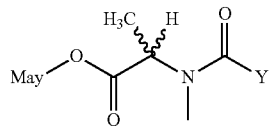

(IV-D,L)

wherein Y represents $(CR_7R_8)_l(CR_5R_6)_m(CR_3R_4)_n$ $CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, and wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl.

Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, and $R_8$ are each H, l and m are each 1, n is 0, and Z is H, (b) $R_1$ and $R_2$ are methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Additional preferred maytansines also include compounds represented by formula (V):

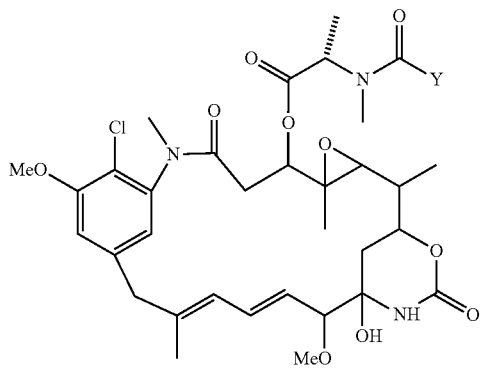

(V)

wherein Y represents $(CR_7R_8)_l(CR_5R_6)_m(CR_3R_4)_n$ $CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, $R_8$ are each H, l and m are 1; n is 0; and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Still further preferred maytansines include compounds represented by formula (VI-L), (VI-D), or (VI-D,L):

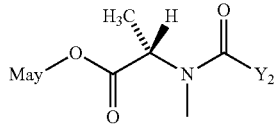

(VI-L)

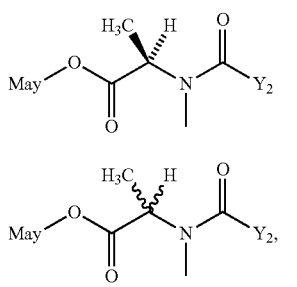

(VI-D)

(VI-D, L)

wherein Y$_2$ represents $(CR_7R_8)_l(CR_5R_6)_m(CR_3R_4)_n$ $CR_1R_2SZ_2$, wherein R$_1$ and R$_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein R$_2$ also can be H, wherein R$_3$, R$_4$, R$_5$, R$_6$, R$_7$, and R$_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, and n are each independently an integer of from 1 to 5, and in addition n can be zero, wherein Z$_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical, and wherein May is a maytansinoid.

Additional preferred maytansines include compounds represented by formula (VII):

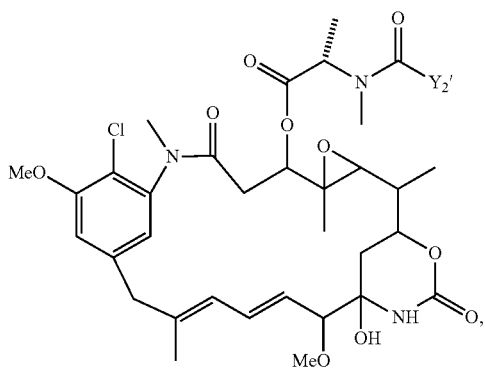

(VII)

wherein Y$_2$' represents $(CR_7R_8)_l(CR_9=CR_{10})_p(C\equiv C)_qA_o$ $(CR_5R_6)_mD_u(CR_{11}=CR_{12})_r(C\equiv C)_sB_t(CR_3R_4)_nCR_1R_2SZ_2$, wherein R$_1$ and R$_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition R$_2$ can be H, wherein A, B, and D each independently is cycloalkyl or cycloalkenyl having 3 to 10 carbon atoms, simple or substituted aryl, or heterocyclic aromatic or heterocycloalkyl radical, wherein R$_3$, R$_4$, R$_5$, R$_6$, R$_7$, R$_8$, R$_9$, R$_{10}$, R$_{11}$, and R$_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, n, o, p, q, r, s, and t are each independently zero or an integer of from 1 to 5, provided that at least two of l, m, n, o, p, q, r, s and t are not zero at any one time, and wherein Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (VII) include compounds of formula (VII), wherein R$_1$ is H and R$_2$ is methyl.

In addition to maytansinoids, the cytotoxic agent used in the conjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

A preferred taxane for use in the preparation of a cytotoxic conjugate is the taxane of formula (VIII):

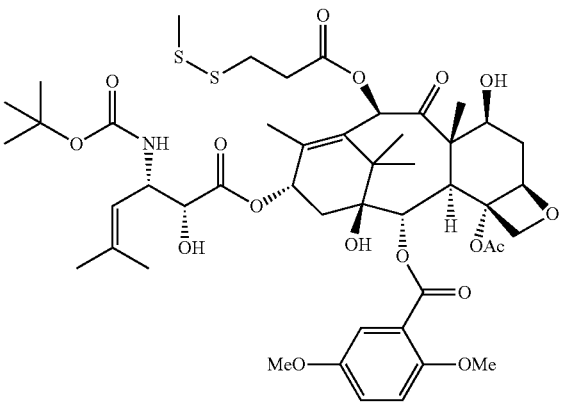

(VIII)

Methods for synthesizing taxanes that can be used in the context of the invention, along with methods for conjugating taxanes to cell-binding agents such as antibodies, are described in detail in U.S. Pat. Nos. 5,416,064, 5,475,092, 6,340,701, 6,372,738, 6,436,931, 6,596,757, 6,706,708, 6,716,821, and 7,390,898.

The cytotoxic agent also can be CC-1065 or a derivative thereof. CC-1065 is a potent anti-tumor antibiotic isolated from the culture broth of *Streptomyces zelensis*. CC-1065 is about 1000-fold more potent in vitro than commonly used anti-cancer drugs, such as doxorubicin, methotrexate, and vincristine (Bhuyan et al., *Cancer Res.*, 42: 3532-3537 (1982)). CC-1065 and its analogs are disclosed in U.S. Pat. Nos. 5,585,499, 5,846,545, 6,340,701, and 6,372,738. The cytotoxic potency of CC-1065 has been correlated with its alkylating activity and its DNA-binding or DNA-intercalating activity. These two activities reside in separate parts of the molecule. In this respect, the alkylating activity is contained in the cyclopropapyrroloindole (CPI) subunit and the DNA-binding activity resides in the two pyrroloindole subunits of CC-1065.

Several CC-1065 analogs are known in the art and also can be used as the cytotoxic agent in the conjugate (see, e.g., Warpehoski et al., *J. Med. Chem.*, 31: 590-603 (1988)). A series of CC-1065 analogs has been developed in which the CPI moiety is replaced by a cyclopropabenzindole (CBI) moiety (Boger et al., *J. Org. Chem.*, 55: 5823-5833 (1990), and Boger et al., *Bioorg. Med. Chem. Lett.*, 1: 115-120 (1991)). These CC-1065 analogs maintain the high in vitro potency of the parental drug, without causing delayed toxicity in mice. Like CC-1065, these compounds are alkylating agents that covalently bind to the minor groove of DNA to cause cell death.

The therapeutic efficacy of CC-1065 analogs can be greatly improved by changing the in vivo distribution through targeted delivery to a tumor site, resulting in lower toxicity to non-targeted tissues, and thus, lower systemic toxicity. To this end, conjugates of analogs and derivatives of CC-1065 with cell-binding agents that specifically target tumor cells have been generated (see, e.g., U.S. Pat. Nos. 5,475,092, 5,585,499, and 5,846,545). These conjugates typically display high target-specific cytotoxicity in vitro, and anti-tumor activity in human tumor xenograft models in mice (see, e.g., Chari et al., *Cancer Res.*, 55: 4079-4084 (1995)).

Methods for synthesizing CC-1065 analogs are described in detail in U.S. Pat. Nos. 5,475,092, 5,585,499, 5,846,545, 6,534,660, 6,586,618, 6,756,397, and 7,329,760.

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs also can be used as the cytotoxic agents of the invention. Doxarubicin and daunorubicin compounds (see, e.g., U.S. Pat. No. 6,630,579) can also be used as the cytotoxic agent.

The cell-binding agent cytotoxic agent conjugates may be prepared by in vitro methods. In order to link a cytotoxic agent to the antibody, a linking group is used. Suitable linking groups are well known in the art and include disulfide groups, acid labile groups, photolabile groups, peptidase labile groups, and esterase labile groups, as well as noncleavable linking groups.

In accordance with the invention, the cell-binding agent is modified by reacting a bifunctional crosslinking reagent with the cell-binding agent, thereby resulting in the covalent attachment of a linker molecule to the cell-binding agent. As used herein, a "bifunctional crosslinking reagent" refers to a reagent that possesses two reactive groups; one of which is capable of reacting with a cell-binding agent, while the other one is capable of reacting with the cytotoxic agent to link the cell-binding agent with the cytotoxic agent, thereby forming a conjugate.

Any suitable bifunctional crosslinking reagent can be used in connection with the invention, so long as the linker reagent provides for retention of the therapeutic, e.g., cytotoxicity, and targeting characteristics of the cytotoxic agent and the cell-binding agent, respectively, while providing an acceptable toxicity profile. Preferably, the linker molecule joins the cytotoxic agent to the cell-binding agent through chemical bonds (as described above), such that the cytotoxic agent and the cell-binding agent are chemically coupled (e.g., covalently bonded) to each other.

In one embodiment, the cell binding agent is chemically coupled to the cytotoxic agent via chemical bonds selected from the group consisting of disulfide bonds, acid labile bonds, photolabile bonds, peptidase labile bonds, and esterase labile bonds.

In one embodiment, the bifunctional crosslinking reagent comprises non-cleavable linkers. A non-cleavable linker is any chemical moiety that is capable of linking a cytotoxic agent, such as a maytansinoid, a taxane, or a CC-1065 analog, to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the cytotoxic agent or the cell-binding agent remains active.

Suitable crosslinking reagents that form non-cleavable linkers between a cytotoxic agent and the cell-binding agent are well known in the art. In one embodiment, the cytotoxic agent is chemically coupled to the cell-binding agent through a thioether bond. In another embodiment, the cytotoxic agent is linked to the cell-binding agent through an amide bond. Examples of non-cleavable linkers include linkers having a maleimido-based moeity or a haloacetyl-based moiety for reaction with the cytotoxic agent. Such bifunctional crosslinking agents are well known in the art (see U.S. Patent Application Publication Nos. 2010/0129314, 2009/0274713, 2008/0050310, 2005/0169933, and Pierce Biotechnology Inc. P.O. Box 117, Rockland, Ill. 61105, USA) and include, but not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-Maleimido-benzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal, and PEG$_n$-Mal. Preferably, the bifunctional crosslinking reagent is SMCC.

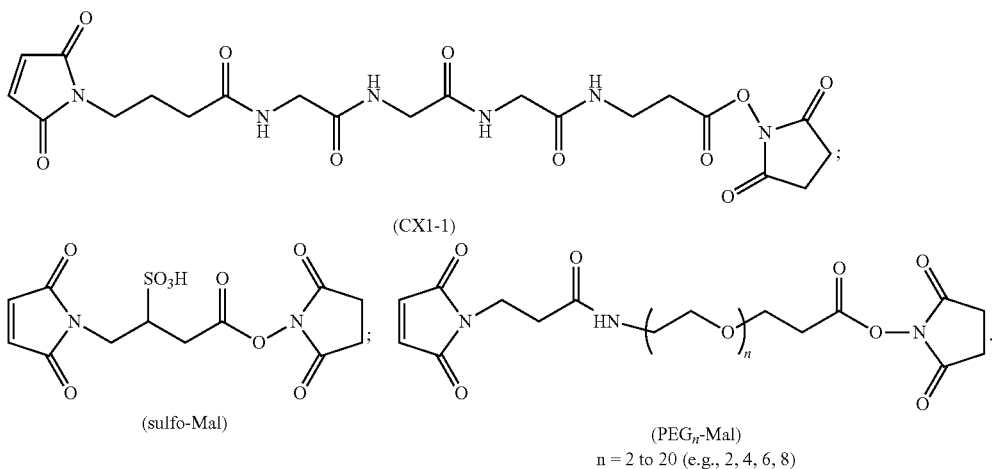

(CX1-1)

(sulfo-Mal)

(PEG$_n$-Mal)
n = 2 to 20 (e.g., 2, 4, 6, 8)

In one embodiment, the linking reagent is a cleavable linker. Examples of suitable cleavable linkers include disulfide containing linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA*, 79: 626-629 (1982), and Umemoto et al., *Int. J. Cancer*, 43: 677-684 (1989)). In one embodiment, the cleavable linker is cleaved under mild conditions, i.e., conditions within a cell under which the activity of the cytotoxic agent is not affected.

In one embodiment, the cytotoxic agent is linked to a cell-binding agent through a disulfide bond. The linker molecule comprises a reactive chemical group that can react with the cell-binding agent. In one embodiment, the bifunctional crosslinking reagent comprises a reactive moiety that can form an amide bond with a lysine residue of the cell-binding agent. Examples of reactive moieties that can form an amide bond with a lysine residue of a cell-binding agent include carboxylic acid moieties and reactive ester moieties, such as N-succinimidyl ester, N-sulfosuccinimidyl ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester.

Preferred reactive chemical groups for reaction with the cell-binding agent are N-succinimidyl esters and N-sulfosuccinimidyl esters. Additionally the linker molecule comprises a reactive chemical group, preferably a dithiopyridyl group, that can react with the cytotoxic agent to form a disulfide bond. Bifunctional crosslinking reagents that enable the linkage of the cell-binding agent with the cytotoxic agent via disulfide bonds are known in the art and include, for example, N-succinimidyl 3-(2-pyridyldithio)propionate (SPDP) (see, e.g., Carlsson et al., *Biochem. J.*, 173: 723-737 (1978)), N-succinimidyl 4-(2-pyridyldithio) butanoate (SPDB) (see, e.g., U.S. Pat. No. 4,563,304), N-succinimidyl 4-(2-pyridyldithio)pentanoate (SPP) (see, e.g., CAS Registry number 341498-08-6), and N-succinimidyl-4-(2-pyridyldithio)2-sulfo butanoate (sulfo-SPDB) (see, e.g., U.S. Patent Application Publication No. 20090274713). Other bifunctional crosslinking reagents that can be used to introduce disulfide groups are known in the art and are described in U.S. Pat. Nos. 6,913,748, 6,716,821 and U.S. Patent Application Publication Nos. 2009/0274713 and 2010/0129314, all of which are incorporated herein in its entirety by reference.

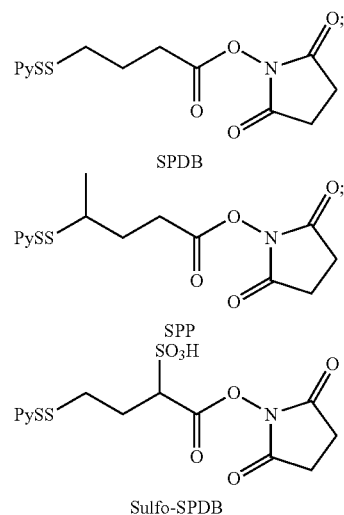

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

HOOC—X$_l$—Y$_n$—Z$_m$—COOH　　(IX), wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication No. 20050169933 A1.

Final purified cell-binding agent cytotoxic agent conjugates produced by the inventive process comprise a cytotoxic agent, a bifunctional crosslinking agent, and a cell-binding agent. In a preferred embodiment of the invention, the cytotoxic agent is DM1, the bifunctional crosslinking agent is SMCC, and the cell-binding agent is huCD37-3 antibody. In another preferred embodiment of the invention, the cytotoxic agent is DM1, the bifunctional crosslinking agent is SMCC, and the cell-binding agent is EGFR-7R antibody. In a preferred embodiment of the invention, the cytotoxic agent is DM1, the bifunctional crosslinking agent is SMCC, and the cell-binding agent is an anti-EFGRvIII antibody. In a preferred embodiment of the invention, the cytotoxic agent is DM1, the bifunctional crosslinking agent is SMCC, and the cell-binding agent is an anti-CD27L antibody. In a preferred embodiment of the invention, the cytotoxic agent is DM1, the bifunctional crosslinking agent is SMCC, and the cell-binding agent is trastuzumab.

The following examples further illustrate the invention but, of course, should not be construed as in any way limiting its scope.

Example 1

This example demonstrates a process for preparing a purified cell-binding agent cytotoxic agent conjugate comprising subjecting a mixture comprising a cell-binding agent cytotoxic agent conjugate and one or more impurities to a PVDF membrane to remove at least a portion of the impurities from the mixture, thereby providing a purified cell-binding agent cytotoxic agent conjugate.

An antibody-SMCC-DM1 conjugate was prepared by the one-step process (as described in U.S. Patent Application Publication No. 20120253021). The reaction mixture was continuously pumped through a PVDF filter and the filtrate was collected and analyzed for DM1 dimer species. As shown in FIG. 1, DM1 dimer species, including DM1-DM1 and DM1-MCC-DM1, that were present prior to the PVDF filtration (see FIG. 1A), were efficiently removed by PVDF filtration (see FIG. 1B).

The results of the experiments reflected in this example demonstrate that PVDF filtration can effectively remove free cytotoxic agent, such as cytotoxic agent dimers, from a mixture comprising a cell-binding agent cytotoxic agent conjugate and one or more impurities.

Example 2

This example demonstrates a process for preparing a purified cell-binding agent cytotoxic agent conjugate comprising subjecting a mixture comprising a cell-binding agent cytotoxic agent conjugate and one or more impurities to a PVDF membrane alone and in combination with an ion exchange chromatography membrane to remove at least a portion of the impurities from the mixture, thereby providing a purified cell-binding agent cytotoxic agent conjugate.

An antibody-SMCC-DM1 conjugate was prepared by the one-step process (as described in U.S. Patent Application Publication No. 2012/0253021). The reaction mixture was filtered through a PVDF membrane filter or a combination of PVDF membrane filter and a Q membrane (an ion exchange chromatography membrane). As shown in Table 1 below, the combination of a PVDF membrane filter and Q membrane removed more DM1 dimer species than the PVDF membrane filter alone.

TABLE 1

|  | RXN | PVDF | PVDF, Q | Q, PVDF |
|---|---|---|---|---|
| DM1-DM1% (over total free DM1 species) | 6.8 | 1.9 | 0.8 | 0.6 |
| DM1-MCC-DM1% (over total free DM1 species) | 19.2 | 6.6 | 2.3 | 1.5 |

The results of the experiments reflected in this example demonstrate that PVDF filtration, when used either alone or in combination with a Q membrane can effectively remove free cytotoxic agent, such as cytotoxic agent dimers, from a mixture comprising a cell-binding agent cytotoxic agent conjugate and one or more impurities.

Example 3

This example demonstrates a process for preparing a purified cell-binding agent cytotoxic agent conjugate comprising repeatedly subjecting a mixture comprising a cell-binding agent cytotoxic agent conjugate and one or more impurities to a PVDF membrane to remove at least a portion of the impurities from the mixture, thereby providing a purified cell-binding agent cytotoxic agent conjugate.

An antibody-SMCC-DM1 conjugate was prepared by the one-step process (as described in U.S. Patent Application Publication No. 2012/0253021). The reaction mixture was filtered through a PVDF membrane filter either two or three times. The percent of DM1 dimers (DM1-DM1 and DM1-MCC-DM1) was measured before and after each filtration. As shown in FIG. 2, additional PVDF membrane filtration can further remove the DM1 dimer species.

The results of the experiments reflected in this example demonstrate that PVDF filtration can effectively remove free cytotoxic agent, such as cytotoxic agent dimers, from a mixture comprising a cell-binding agent cytotoxic agent conjugate and one or more impurities.

Example 4

This example demonstrates a process for preparing a purified cell-binding agent cytotoxic agent conjugate comprising subjecting a mixture comprising a cell-binding agent cytotoxic agent conjugate and one or more impurities to a PVDF membrane to remove at least a portion of the impurities from the mixture, thereby providing a purified cell-binding agent cytotoxic agent conjugate.

An huN901-SPP-DM1 conjugate was prepared by the one-step process (as described in U.S. Patent Application Publication No. 2012/0253021). Briefly, huN901 antibody was diafiltered into modification buffer (50 mM potassium phosphate, 2 mM EDTA, pH 7.5) and then conjugated at 2.5 mg/ml with 1.55 molar excess DM1 relative to linker and 7 moles SPP linker relative to antibody, at ambient temperature for 24-28 hours in 50 mM potassium phosphate, 2 mM EDTA, pH 7.5 buffer containing 10% (v/v) DMA.

The reaction mixture was then filtered through a 0.22 μm Dura pore PVDF filter. The amount of free cytotoxic agent present in the reaction mixture before and after PVDF filtration was measured by HPLC. The results are shown in Table 3 below.

TABLE 3

| Free Cytotoxic Agent Species | % Free Cytotoxic Agent Species | |
|---|---|---|
| | Before PVDF filtration | After PVDF filtration |
| DM1 | 8.8% | 7.6% |
| DM1-TPA | 9.4% | 7.6% |
| DM1-SPP | 1.3% | 0.2 |
| DM1-DM1 | 24.1% | 2.1 |
| DM1-SPP-DM1 | 23.8% | 3.5 |

As shown in Table 3, the amount of all free cytotoxic agent species measured (i.e., DM1, DM1-TPA, DM1-SPP, DM1-DM1, and DM1-SPP-DM1) was reduced by PVDF filtration. In particular, both cytotoxic agent dimer species, DM1-DM1 and DM1-SPP-DM1, were significantly reduced by the PVDF filtration.

The results of the experiments reflected in this example demonstrate that PVDF filtration can effectively remove free cytotoxic agent from a mixture comprising a cell-binding agent cytotoxic agent conjugate and one or more impurities.

Example 5

This example demonstrates a process for preparing a purified cell-binding agent cytotoxic agent conjugate comprising subjecting a mixture comprising a cell-binding agent cytotoxic agent conjugate and one or more impurities to a PVDF membrane to remove at least a portion of the impurities from the mixture, thereby providing a purified cell-binding agent cytotoxic agent conjugate.

HuN901 antibody was modified at a concentration of 16.0 mg/ml with SPP at a ratio of 11.0 mg/g antibody (4.7× molar ratio) in 50 mM KPi, 50 mM KCl, 2 mM EDTA, pH 7.5 buffer with 5% (v/v) DMA for a total of 180 minutes at 23° C. with constant stirring. The modified antibody was then conjugated at a concentration of 2.5 mg/ml with a 1.8 fold molar excess of DM1 relative to initial SPP linker in 15 mM KPi buffer with 2 mM EDTA, 7.7 mM citric acid and 5% DMA at pH 5.3 for 23 hrs at 23° C. with constant stirring. Then the reaction mixture was filtered through a 0.22 μm Dura pore PVDF filter. The amount of free cytotoxic agent present in the reaction mixture before and after PVDF filtration was measured by HPLC. The results are shown in Table 4 below.

TABLE 4

| Free Cytotoxic Agent Species | % Free Cytotoxic Agent Species | |
|---|---|---|
| | Before filtration | After filtration |
| DM1-TPA | 36.7% | 21.2% |
| DM1 | 6.6% | 0.4% |
| DM1-DM1 | 8.8% | 0.06% |
| DM1-SPP-DM1 | 0.1% | Not detectable |

As shown in Table 4, the amount of all free cytotoxic agent species measured (i.e., DM1-TPA, DM1, DM1-DM1, and DM1-SPP-DM1) was reduced by PVDF filtration. In particular, both cytotoxic agent dimer species, DM1-DM1 and DM1-SPP-DM1, were significantly reduced by the PVDF filtration.

The results of the experiments reflected in this example demonstrate that PVDF filtration can effectively remove free cytotoxic agent from a mixture comprising a cell-binding agent cytotoxic agent conjugate and one or more impurities.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing a purified cell-binding agent cytotoxic agent conjugate comprising:
   (a) contacting a cell-binding agent with a cytotoxic agent to form a first mixture comprising the cell-binding agent and the cytotoxic agent, then contacting the first mixture with a bifunctional crosslinking reagent comprising a linker, in a solution having a pH of about 4 to about 9, to provide a second mixture comprising the cell-binding agent cytotoxic agent conjugate comprising the cell-binding agent chemically coupled through the linker to the cytotoxic agent and one or more impurities;
   (b) adjusting the second mixture to have a pH of about 7 to about 9 to form a pH-adjusted second mixture;
   (c) subjecting the pH-adjusted second mixture to a polyvinyl difluoride (PVDF) membrane to remove at least a portion of the impurities, thereby providing a purified second mixture of the cell-binding agent cytotoxic agent conjugate; and
   (d) subjecting the purified second mixture after step (c) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture.

2. The process of claim 1, wherein step (c) is sequentially repeated two, three, or four times prior to step (d).

3. The process of claim 1, wherein adsorptive chromatography is utilized in step (d).

4. The process of claim 1, wherein the adsorptive chromatography is selected from hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof.

5. The process of claim 4, wherein the adsorptive chromatography is ion exchange chromatography.

6. The process of claim 5, wherein the ion exchange chromatography is ceramic hydroxyapatite (CHT) chromatography.

7. The process of claim 1, wherein tangential flow filtration is utilized in step (d).

8. The process of claim 1, wherein the contacting in step (a) is effected by providing the cell-binding agent in a reaction vessel, adding the cytotoxic agent to the reaction vessel to form the first mixture comprising the cell-binding agent and the cytotoxic agent, and then adding the bifunctional crosslinking reagent to the first mixture.

9. The process of claim 1, further comprising holding the mixture between steps (a)-(b), steps (b)-(c), or steps (c)-(d) to release the unstably bound linkers from the cell-binding agent.

10. The process of claim 9, wherein the mixture is held for about 20 hours at a temperature of about 2° C. to about 8° C.

11. The process of claim 1, further comprising quenching the second mixture between steps (a)-(b) to quench any unreacted cytotoxic agent and/or unreacted bifunctional crosslinking reagent.

12. The process of claim 11, wherein the mixture is quenched by contacting the second mixture with a quenching reagent that reacts with the unreacted cytotoxic reagent.

13. The process of claim 12, wherein the quenching reagent is selected from 4-maleimidobutyric acid, 3-maleimidopropionic acid, N-ethylmaleimide, iodoacetamide, and iodoacetamidopropionic acid.

14. The process of claim 1, wherein the process further comprises subjecting the mixture to an ion exchange chromatography membrane between steps (a) and (b) or steps (b) and (c).

15. The process of claim 1, wherein the process further comprises subjecting the mixture to an ion exchange chromatography membrane between steps (c) and (d).

16. The process of claim 1, wherein the one or more impurities are selected from the group of cytotoxic agent dimers, aggregates of the cell-binding agent cytotoxic agent conjugate, free cytotoxic agent, unconjugated linker, and mixtures thereof.

17. The process of claim 16, wherein the mixture comprises aggregates of the cell-binding agent cytotoxic agent conjugate as an impurity, and some portion of the aggregates of the cell-binding agent cytotoxic agent conjugate is removed from the mixture to provide the purified cell-binding agent cytotoxic agent conjugate.

18. The process of claim 16, wherein the mixture comprises free cytotoxic agent as an impurity, and some portion of the free cytotoxic agent is removed from the mixture to provide the purified cell-binding agent cytotoxic agent conjugate.

19. The process of claim 16, wherein the mixture comprises unconjugated linker as an impurity, and some portion of the unconjugated linker is removed from the mixture to provide the purified cell-binding agent cytotoxic agent conjugate.

20. The process of claim 1, wherein the pH of the pH-adjusted second mixture is about 7 to about 8.

21. The process of claim 1, wherein the pH of the pH-adjusted second mixture is about 8 to about 9.

22. The process of claim 21, wherein the pH of the pH-adjusted second mixture is about 8.5.

23. The process of claim 1, wherein at least 50% of the one or more impurities are removed from the pH-adjusted second mixture.

24. The process of claim 1, wherein at least 75% of the one or more impurities are removed from the pH-adjusted second mixture.

25. The process of claim 1, wherein at least 90% of the one or more impurities are removed from the pH-adjusted second mixture.

26. The process of claim 1, wherein the PVDF membrane is selected from a 0.22 micron pore size membrane, a 0.45 micron pore size membrane, and a dual layer 0.45/0.22 micron pore size membrane.

27. The process of claim 1, wherein the PVDF membrane is gamma irradiated.

28. The process of claim 1, wherein the contacting in step (a) occurs in a solution having a pH of about 7 to about 9.

29. The process of claim 1, wherein the solution in step (a) comprises a buffering agent selected from a citrate buffer, an acetate buffer, a succinate buffer, and a phosphate buffer.

30. The process of claim 28, wherein the solution in step (a) comprises a buffering agent selected from HEPPSO (N-(2-Hydroxyethyl)piperazine-N'-(2-hydroxypropanesulfonic acid)), POPSO (Piperazine-1,4-bis-(2-hydroxy-propane-sulfonic acid) dihydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

31. The process of claim 1, wherein the contacting in step (a) occurs at a temperature of about 16° C. to about 24° C.

32. The process of claim 1, wherein the contacting in step (a) occurs at a temperature of about 0° C. to about 15° C.

33. The process of claim 1, wherein the bifunctional crosslinking reagent is an acid labile linker, a disulfide containing linker, a photolabile linker, a peptidase labile linker, or an esterase labile linker.

34. The process of claim 1, wherein the bifunctional crosslinking reagent is a disulfide-containing cleavable linker.

35. The process of claim 1, wherein the bifunctional crosslinking reagent is a non-cleavable linker.

36. The process of claim 1, wherein the bifunctional crosslinking reagent comprises an N-succinimidyl ester moiety, an N-sulfosuccinimidyl ester moiety, a maleimido-based moiety, or a haloacetyl-based moiety.

37. The process of claim 34, wherein the bifunctional crosslinking reagent is selected from N-succinimidyl 3-(2-pyridyldithio)propionate (SPDP), N-succinimidyl 4-(2-pyridyldithio)butanoate (SPDB), N-succinimidyl 4-(2-pyridyldithio)pentanoate (SPP), and N-succinimidyl-4-(2-pyridyldithio)2-sulfo butanoate (sulfo-SPDB).

38. The process of claim 35, wherein the bifunctional crosslinking reagent is selected from N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), β-maleimidopropyloxy-succinimidyl ester (BMPS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI), sulfo-Mal, $PEG_4$-Mal and CX1-1.

39. The process of claim 1, wherein the cell-binding agent is selected from antibodies, interferons, interleukin 2 (IL-2), interleukin 3 (IL-3), interleukin 4 (IL-4), interleukin 6 (IL-6), insulin, epidermal growth factor (EGF), transforming growth factor alpha (TGF-α), fibroblast growth factor (FGF), vascular endothelial growth factor (VEGF), a colony stimulating factor (G-CSF, MCSF, GM-CSF), and transferrin.

40. The process of claim 39, wherein the cell-binding agent is an antibody.

41. The process of claim 40, wherein the antibody is a monoclonal antibody.

42. The process of claim 41, wherein the antibody is a humanized monoclonal antibody.

43. The process of claim 39, wherein the cell-binding agent is an antibody selected from huB4, huC242, trastuzumab, bivatuzumab, sibrotuzumab, huDS6, rituximab, anti-CD33 antibody, anti-CD27L antibody, anti-Her2 antibody, anti-epidermal growth factor receptor (EGFR) antibody, anti-EGFRvIII antibody, Cripto, anti-CD138 antibody, anti-CD38 antibody, anti-ephrin type A receptor 2 (EphA2) antibody, integrin targeting antibody, anti-CD37 antibody, anti-folate receptor antibody, anti-Her3 antibody, B-B4 antibody and anti-insulin like growth factor I receptor (IGFIR) antibody.

44. The process of claim 1, wherein the cytotoxic agent is selected from maytansinoids, taxanes, and CC1065.

45. The process of claim 44, wherein the cytotoxic agent is a maytansinoid.

46. The process of claim 45, wherein the maytansinoid comprises a thiol group.

47. The process of claim 46, wherein the maytansinoid is $N^{2'}$-deacetyl-$N^{2'}$-(3-mercapto-1-oxopropyl)-maytansine (DM1) or $N^{2'}$-deacetyl-$N^{2'}$-(4-methyl-4-mercapto-1-oxopentyl)-maytansine (DM4).

48. The process of claim 1, wherein the cytotoxic agent is DM1, the bifunctional crosslinking agent is SMCC, and the cell-binding agent is huCD37-3 antibody.

49. The process of claim 1, wherein the cytotoxic agent is DM1, the bifunctional crosslinking agent is SMCC, and the cell-binding agent is EGFR-7R antibody.

50. The process of claim 1, wherein the cytotoxic agent is DM1, the bifunctional crosslinking agent is SMCC, and the cell-binding agent is an anti-EFGRvIII antibody.

51. The process of claim 1, wherein the cytotoxic agent is DM1, the bifunctional crosslinking agent is SMCC, and the cell-binding agent is an anti-CD27L antibody.

52. The process of claim 1, wherein the cytotoxic agent is DM1, the bifunctional crosslinking agent is SMCC, and the cell-binding agent is trastuzumab.

53. The process of claim 1, wherein the process further comprises
   (a) contacting a cell-binding agent with a cytotoxic agent to form a first mixture comprising the cell-binding agent and the cytotoxic agent, then contacting the first mixture with a bifunctional crosslinking reagent comprising a linker, in a solution having a pH of about 4 to about 9, to provide a second mixture comprising the cell-binding agent cytotoxic agent conjugate comprising the cell-binding agent chemically coupled through the linker to the cytotoxic agent and one or more impurities;
   (b) adjusting the second mixture to have a pH of about 7 to about 9 to form a pH-adjusted second mixture;
   (c) subjecting the pH-adjusted second mixture to a PVDF membrane to remove at least a portion of the impurities from the mixture, thereby providing a purified second mixture of the cell-binding agent cytotoxic agent conjugate;
   (d) quenching the purified second mixture after step (c) to quench any unreacted cytotoxic agent and/or unreacted bifunctional crosslinking reagent;
   (e) subjecting the quenched mixture after step (d) to a PVDF membrane to remove at least a portion of the impurities from the mixture, thereby providing a purified third mixture of the cell-binding agent cytotoxic agent conjugate;
   (f) holding the purified third mixture to release the unstably bound linkers from the cell-binding agent;
   (g) optionally subjecting the purified third mixture after step (f) to a PVDF membrane to remove at least a portion of the impurities from the mixture, thereby providing a purified fourth mixture of the cell-binding agent cytotoxic agent conjugate; and
   (h) subjecting the purified fourth mixture after step (g) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture.

54. The process of claim 53, wherein the pH-adjusted second mixture has a pH of about 8.5.

55. The process of claim 54, wherein the quenched mixture of step (e) has a pH of about 4.8.

56. A process for preparing a purified cell-binding agent cytotoxic agent conjugate comprising:
   (a) contacting a cell-binding agent with a bifunctional crosslinking reagent to covalently attach a linker to the cell-binding agent and thereby prepare a first mixture comprising cell-binding agents having linkers bound thereto,
   (b) subjecting the first mixture to tangential flow filtration, selective precipitation, non-adsorptive chromatography, adsorptive filtration, adsorptive chromatography, or a combination thereof and thereby prepare a purified first mixture of cell-binding agents having linkers bound thereto,
   (c) conjugating a cytotoxic agent to the cell-binding agents having linkers bound thereto in the purified first mixture by reacting the cell-binding agents having linkers bound thereto with a cytotoxic agent in a solution having a pH of about 4 to about 9 to prepare a second mixture comprising the cell-binding agent-cytotoxic agent conjugate comprising the cell-binding agent chemically coupled to the cytotoxic agent through the linker, and further comprising one or more impurities,
   (d) adjusting the second mixture to have a pH of about 7 to about 9 to form a pH-adjusted second mixture,
   (e) subjecting the pH-adjusted second mixture to a polyvinyl difluoride (PVDF) membrane to remove at least a portion of the impurities, thereby providing a purified second mixture of the cell-binding agent cytotoxic agent conjugate; and
   subjecting the purified second mixture after step (e) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture.

57. The process of claim 56, wherein step (e) is sequentially repeated two, three, or four times prior to step (f).

58. The process of claim 56, wherein the process further comprises subjecting the mixture to an ion exchange chromatography membrane between steps (c) and (d) or steps (d) and (e).

59. The process of claim 56, wherein the process further comprises subjecting the mixture to an ion exchange chromatography membrane between steps (e) and (f).

60. The process of claim 56, wherein adsorptive chromatography is utilized in steps (b) and (f).

61. The process of claim 56, wherein tangential flow filtration is utilized in step (b) and adsorptive chromatography is utilized in step (f).

62. The process of claim 56, wherein adsorptive chromatography is utilized in step (b) and tangential flow filtration is utilized in step (f).

63. The process of claim 56, wherein the adsorptive chromatography is selected from hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof.

64. The process of claim 63, wherein the adsorptive chromatography is ion-exchange chromatography.

65. The process of claim 64, wherein the ion-exchange chromatography is ceramic hydroxyapatite (CHT) chromatography.

66. The process of claim 56, wherein tangential flow filtration is utilized in steps (b) and (f).

67. The process of claim 56, wherein non-adsorptive chromatography is utilized in steps (b) and (f).

68. The process of claim 56, wherein the solution in step (c) comprises sucrose.

69. The process of claim 56, wherein the solution in step (c) comprises a buffering agent selected from a citrate buffer, an acetate buffer, a succinate buffer, and a phosphate buffer.

70. The process of claim 56, wherein the solution in step (c) comprises a buffering agent selected from HEPPSO (N-(2-Hydroxyethyl)piperazine-N'-(2-hydroxypropanesulfonic acid)), POPSO (Piperazine-1,4-bis-(2-hydroxy-propane-sulfonic acid) dihydrate), HEPES (4-(2-hydroxyethyl) piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

71. The process of claim 56, further comprising
(g) holding the mixture between at least one of steps (a)-(b), steps (b)-(c), steps (c)-(d), steps (d)-(e), and steps (e)-(f) to release the unstably bound linkers from the cell-binding agent.

72. A process for preparing a purified cell-binding agent cytotoxic agent conjugate comprising:
(a) contacting a cell-binding agent with a bifunctional crosslinking reagent to covalently attach a linker to the cell-binding agent and thereby prepare a first mixture comprising cell-binding agents having linkers bound thereto;
(b) conjugating a cytotoxic agent to the cell-binding agents having linkers bound thereto in the first mixture by reacting the cell-binding agents having linkers bound thereto with a cytotoxic agent to prepare a second mixture comprising the cell-binding agent-cytotoxic agent conjugate comprising the cell-binding agent chemically coupled through the linker to the cytotoxic agent and one or more impurities;
(c) adjusting the second mixture to have a pH of about 7 to about 9 to form a pH-adjusted second mixture;
(d) subjecting the pH-adjusted second mixture to a polyvinyl difluoride (PVDF) membrane to remove at least a portion of the impurities, thereby providing a purified second mixture of the cell-binding agent cytotoxic agent conjugate; and
(e) subjecting the purified second mixture after step (d) to tangential flow filtration, selective precipitation, non-adsorptive chromatography, adsorptive filtration, adsorptive chromatography, or a combination thereof, to further purify the cell-binding agent-cytotoxic agent conjugate from the impurities and thereby prepare a purified third mixture of the cell-binding agent-cytotoxic agent conjugate, wherein the purified third mixture comprises a reduced amount of the impurities as compared to the purified second mixture.

73. The process of claim 72, wherein the first mixture is not subjected to purification between steps (a) and (b).

74. The process of claim 72, wherein step (d) is sequentially repeated two, three, or four times prior to step (e).

75. The process of claim 72, wherein the process further comprises subjecting the mixture to an ion exchange chromatography membrane between steps (b) and (c) or steps (c) and (d).

76. The process of claim 72, wherein the process further comprises subjecting the mixture to an ion exchange chromatography membrane between steps (d) and (e).

77. The process of claim 72, wherein adsorptive chromatography is utilized in step (e).

78. The process of claim 77, wherein the adsorptive chromatography is selected from hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof.

79. The process of claim 78, wherein the adsorptive chromatography is ion-exchange chromatography.

80. The process of claim 79, wherein the ion-exchange chromatography is ceramic hydroxyapatite (CHT) chromatography.

81. The process of claim 72, wherein tangential flow filtration is utilized in step (e).

82. The process of claim 72, wherein non-adsorptive chromatography is utilized in step (e).

83. The process of claim 72, wherein the solution in step (b) comprises sucrose.

84. The process of claim 72, wherein the solution in step (b) comprises a buffering agent selected from a citrate buffer, an acetate buffer, a succinate buffer, and a phosphate buffer.

85. The process of claim 72, wherein the solution in step (b) comprises a buffering agent selected from HEPPSO (N-(2-Hydroxyethyl)piperazine-N'-(2-hydroxypropanesulfonic acid)), POPSO (Piperazine-1,4-bis-(2-hydroxy-propane-sulfonic acid) dihydrate), HEPES (4-(2-hydroxyethyl) piperazine-1-ethanesulfonic acid), HEPPS (EPPS) (4-(2- hydroxyethyl)piperazine-1-propanesulfonic acid), TES (N-[tris(hydroxymethyl)methyl]-2-aminoethanesulfonic acid), and a combination thereof.

86. The process of claim 72, further comprising
(f) holding the mixture between at least one of steps (a)-(b), steps (b)-(c), steps (c)-(d), and steps (d)-(e) to release the unstably bound linkers from the cell-binding agent.

87. The process of claim 86, wherein the mixture comprises cytotoxic agent dimers as an impurity, and some portion of the cytotoxic agent dimers is removed from the mixture to provide the purified cell-binding agent cytotoxic agent conjugate.

88. The process of claim 87, wherein the cytotoxic agent dimer comprises

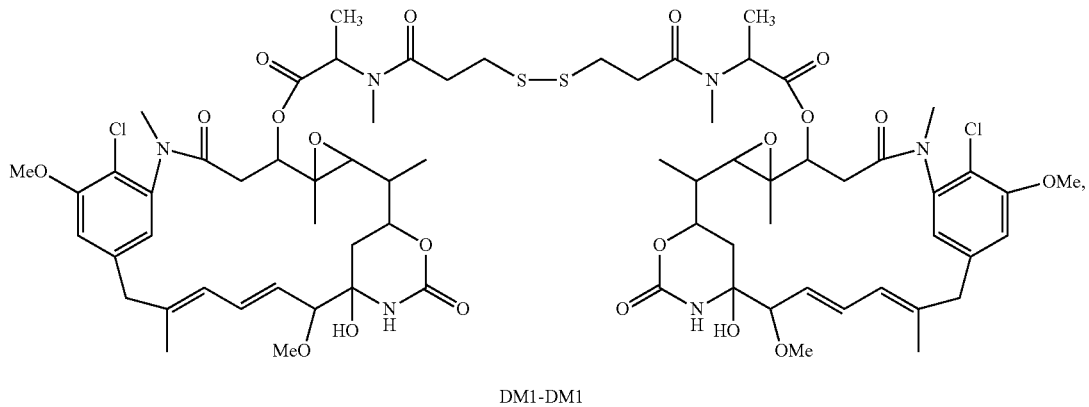

DM1-DM1

89. The process of claim 87, wherein the cytotoxic agent dimer comprises

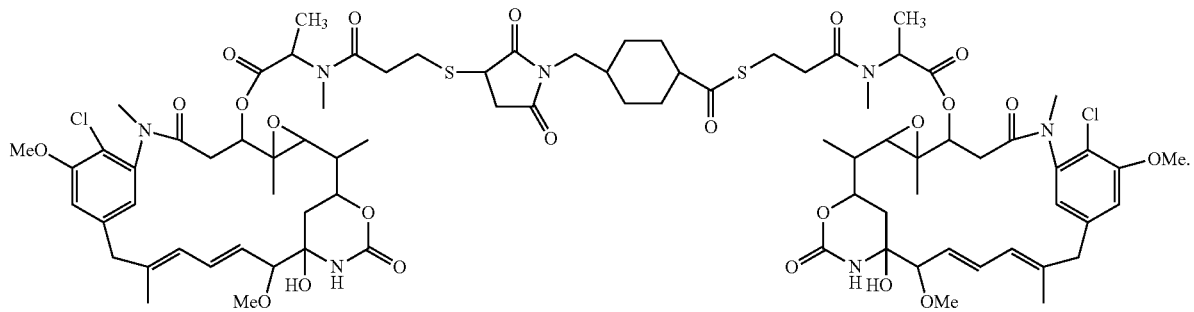

DM1-MCC-DM1

90. The process of claim 87, wherein the cytotoxic agent dimer comprises

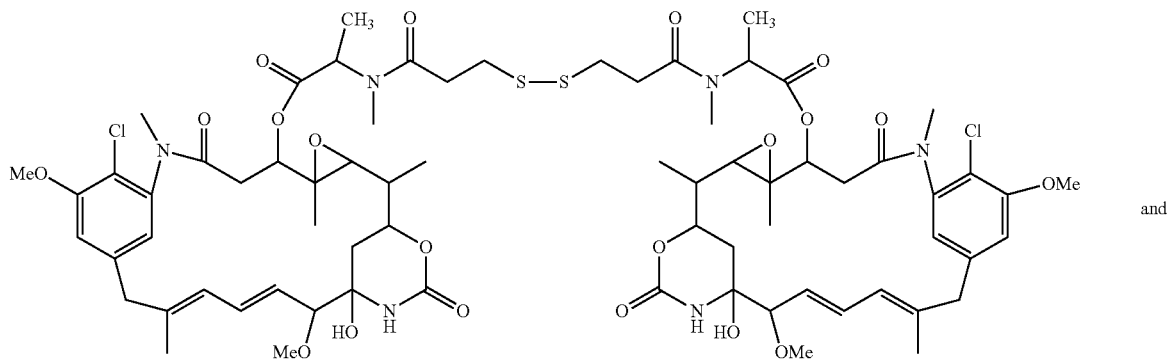

and

DM1-DM1

61
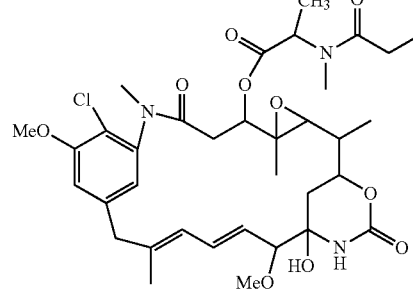
-continued
62
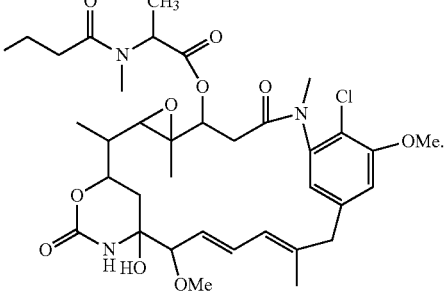
DM1-MCC-DM1
* * * * *